US006594432B2

(12) United States Patent
Chen et al.

(10) Patent No.: US 6,594,432 B2
(45) Date of Patent: Jul. 15, 2003

(54) MICROARRAY FABRICATION TECHNIQUES AND APPARATUS

(75) Inventors: Shiping Chen, Rockville, MD (US); Yuling Luo, Castro Valley, CA (US)

(73) Assignee: GenoSpectra, Inc., Fremont, CA (US)

( * ) Notice: Subject to any disclaimer, the term of this patent is extended or adjusted under 35 U.S.C. 154(b) by 0 days.

(21) Appl. No.: 09/791,994

(22) Filed: Feb. 22, 2001

(65) Prior Publication Data

US 2002/0051979 A1 May 2, 2002

Related U.S. Application Data

(60) Provisional application No. 60/244,711, filed on Oct. 30, 2000, provisional application No. 60/220,085, filed on Jul. 21, 2000, provisional application No. 60/216,265, filed on Jul. 6, 2000, provisional application No. 60/188,872, filed on Mar. 13, 2000, and provisional application No. 60/183,737, filed on Feb. 22, 2000.

(51) Int. Cl.[7] ............................ G02B 6/00; G02B 6/02; C12M 1/00
(52) U.S. Cl. ..................... 385/133; 385/127; 436/518; 433/29; 435/287.1
(58) Field of Search ............................... 385/133, 127; 436/518; 433/29; 435/287.1

(56) References Cited

U.S. PATENT DOCUMENTS

| 4,010,019 A | 3/1977 | Cole et al. | |
|---|---|---|---|
| 4,877,745 A | 10/1989 | Hayes et al. | |
| 4,981,783 A | 1/1991 | Augenlicht | |
| 5,143,854 A | 9/1992 | Pirrung et al. | |
| 5,265,327 A | 11/1993 | Faris et al. | |
| 5,276,327 A | 1/1994 | Bossen et al. | |
| 5,384,261 A | 1/1995 | Winkler et al. | |
| 5,436,327 A | 7/1995 | Southern et al. | |
| 5,445,934 A | 8/1995 | Fodor et al. | |
| 5,474,796 A | 12/1995 | Brennan | |
| 5,525,464 A | 6/1996 | Drmanac et al. | |
| 5,565,324 A | 10/1996 | Still et al. | |
| 5,593,839 A | 1/1997 | Hubbell et al. | |
| 5,604,587 A | 2/1997 | Che et al. | |
| 5,630,925 A | 5/1997 | Pentoney, Jr. et al. | 204/604 |
| 5,658,802 A | 8/1997 | Hayes et al. | |
| 5,690,894 A | 11/1997 | Pinkel et al. | 422/68.1 |
| 5,700,637 A | 12/1997 | Southern | |
| 5,740,297 A * | 4/1998 | Onishi et al. | 385/127 |
| 5,741,554 A | 4/1998 | Tisone | |
| 5,744,305 A | 4/1998 | Fodor et al. | |
| 5,770,151 A | 6/1998 | Roach et al. | |
| 5,770,367 A | 6/1998 | Southern et al. | |
| 5,770,722 A | 6/1998 | Lockhart et al. | |
| 5,800,992 A | 9/1998 | Fodor et al. | |
| 5,807,522 A | 9/1998 | Brown et al. | |
| 5,831,070 A | 11/1998 | Pease et al. | |
| 5,837,832 A | 11/1998 | Chee et al. | |
| 5,900,481 A | 5/1999 | Lough et al. | |
| 5,919,523 A | 7/1999 | Sundberg et al. | |
| 5,948,624 A | 9/1999 | Rothschild et al. | |
| 6,027,873 A | 2/2000 | Schellenberger et al. | |
| 6,048,695 A | 4/2000 | Bradley et al. | |
| 6,054,270 A | 4/2000 | Southern | |
| 6,083,763 A | 7/2000 | Balch | |
| 6,101,946 A | 8/2000 | Martinsky et al. | |
| 6,110,426 A | 8/2000 | Shalon et al. | |
| 6,136,962 A | 10/2000 | Shi et al. | |
| 6,235,473 B1 | 5/2001 | Friedman et al. | |
| 6,270,342 B1 * | 8/2001 | Neuberger et al. | 433/29 |
| 6,312,976 B1 * | 11/2001 | Ogawa | 436/518 |
| 6,387,331 B1 | 5/2002 | Hunter | 422/102 |
| 2002/0072111 A1 | 6/2002 | Clarkin et al. | 435/287.1 |

FOREIGN PATENT DOCUMENTS

| EP | 0 955 084 A1 | 11/1999 |
|---|---|---|
| EP | 1 157 737 A2 | 11/2001 |
| JP | 07-023995 | 1/1995 |
| JP | 2000-245460 | 9/2000 |
| JP | 2000-245461 | 9/2000 |
| JP | 2000-270877 | 10/2000 |
| JP | 2000-270878 | 10/2000 |
| JP | 2000-270879 | 10/2000 |
| JP | 2000-279177 | 10/2000 |
| JP | 2000-342298 | 12/2000 |

(List continued on next page.)

OTHER PUBLICATIONS

Shalon et al. (1996). "A DNA Microarray System for Analyzing Complex DNA Samples Using Two–Color Fluorescent Probe Hybridization," *Genome Res* 6:639–645.

Zhou et al. (2001). "Solution and Chip Arrays in Protein Profiling," *Trends Biotechnol* 10(Suppl):S34–39.

Eisen, M. B. and Brown, P.O. (1999). "12 DNA Arrays For Analysis of Gene Expression," *Method In Enzymolog*, 303:179–205.

Lashkari D. A. et al. (Nov. 1997). "Yeast Microarrays for Genome Wide Parallel Genetic and Gene Expression Analysis,"*Proc. Natl. Acad. Sci. USA Genetics* 94:13057–13062.

Lemieux, B. et al. (1998). "Overview of DNA Chip Technology," *Molecular Breeding*, 4:277–289.

Schena, M. (1996). "Genome Analysis with Gene Expression Microarrays," *BioEssays* 18(5):427–431.

(List continued on next page.)

*Primary Examiner*—Jeffrey Fredman
(74) *Attorney, Agent, or Firm*—Morrison & Foerster LLP

(57) ABSTRACT

Disclosed is a microarray printing system and methods of printing probe microarrays. The system has a print head formed of one or more bundles of individual capillaries, such as light-guiding capillaries. The bundles may especially be random bundles of capillaries that provide a large number of probes on the surface of a substrate. Methods of registering or correlating the distal and proximal ends of the capillaries are also provided. Further, the invention provides methods and equipment for identifying defective microarrays that are missing one or more probes from the surface of the microarray.

24 Claims, 11 Drawing Sheets

FOREIGN PATENT DOCUMENTS

| | | |
|---|---|---|
| WO | WO 97/18226 A1 | 5/1997 |
| WO | WO 98/29736 A1 | 7/1998 |
| WO | WO 98/55593 A1 | 12/1998 |
| WO | WO 99/34920 | 7/1999 |
| WO | WO 99/40434 A1 | 8/1999 |
| WO | WO 99/55460 A1 | 11/1999 |
| WO | WO 99/55461 A1 | 11/1999 |
| WO | WO 00/01798 A2 | 1/2000 |
| WO | WO 00/01859 A2 | 1/2000 |
| WO | WO 00/01859 A3 | 1/2000 |
| WO | WO 00/13796 A1 | 3/2000 |
| WO | WO 00/43752 A1 | 7/2000 |
| WO | WO 00/50871 A1 | 8/2000 |
| WO | WO 00/53736 A1 | 9/2000 |
| WO | WO 00/53739 A1 | 9/2000 |
| WO | WO 00/62934 A1 | 10/2000 |
| WO | WO 00/66360 A1 | 11/2000 |
| WO | WO 00/76662 A2 | 12/2000 |
| WO | WO 01/06011 A2 | 1/2001 |
| WO | WO 01/30498 A1 | 5/2001 |
| WO | WO 01/31317 A1 | 5/2001 |
| WO | WO 01/31333 A1 | 5/2001 |
| WO | WO 99/13312 | 12/2001 |

OTHER PUBLICATIONS

Schena, M. et al. (Jul. 1998). "Microarrays: Biotechnology's Discovery Platform for Functional Genomics," *TIBTECH* 16(7):301–306.

Yu–Hui R. et al. (1999). "Immobilization of Oligonucleotides Onto A Glass Support Via Disulfide Bonds:A Method For Preparation of DNA Microarrays," *Analytical Biochemistry*, 266(1):23–30.

Ayadim, M. et al. (1995). "Photosensitizers Covalently Anchored to the Silica Surface: Modulation of the Excited State Efficiency through Electron Transfer from the Linking Arm or from the Surface," *Tetrahedron Letts.* 36:4615–4618.

Beier, M. et al. (May 1, 1999). "Versatile Derivatisation of Solid Support Media for Covalent Bonding on DNA–Microchips," *Nucl. Acids Res.* 27(9):1970–1977.

Brown, B.B. et al. (Sep. 1995). "A Single–Bead Decode Strategy Using Electrospray Ionization Mass Spectrometry and a New Photolabile Linker: 3–Amino–3–(2–Nitrophenyl)Propionic Acid," *Molecular Diversity* 1(1):4–12.

Camilleri, P., ed. (1998). *Capillary Electrophoresis: Theory and Practice.* Second Edition. CRC Press; New Yprk, NY., 2 pages total (Table of Contents only).

Dorman, G. et al. (Feb. 2000). "Using Photolabile Ligands in Drug Discovery and Development," *Trends Biotechnol.* 18:64–77.

Hermanson, G.T. (1995). *Bioconjugate Techniques.* Academic Press, pp. ix–xx (Table of Contents only).

Olejnik, J. et al. (Oct. 1996). "Photocleavable Biotin Phosphoramidite for 5'–End–Labeling, Affinity Purification and Phosphorylation of Synthetic Oligonucleotides," *Nucl. Acids Res.* 24(2):361–366.

Pinkel, D. et al. (Oct. 1998). "High Resolution Analysis of DNA Copy Number Variation Using Comparative Genomic Hybridization to Microarrays," *Nat. Genet.* 20:207–211.

Rogers, Y.H. et al. (Jan. 1, 1999). "Immobilization of Oligonucleotides onto a Glass Support via Disulfide Bonds: A Method for Preparation of DNA Microarrays," *Anal. Biochem.* 266(1):23–30.

Sano, T. et al. (Dec. 1991). "A Streptavidin–Protein A Chimera that Allows One–Step Production of a Variety of Specific Antibody Conjugates," *Bio/Technol.* 9:1378–1381.

Schena, M. et al. (Oct. 20, 1995). "Quantitative Monitoring of Gene Expression Patterns with a Complementary DNA Microarray," *Science* 270:467–470.

Wilcheck, M. et al. (1990). "Applications of Avidin–Biotin Technology: Literature Survey," *Meth. Enzymol.* 184:14–45, 529–537, 588–600.

Wong, S.S. (1991). *Chemistry of Protein Conjugation and Cross Linking.* CRC Press; Boston, MA., 7 pages total (Table of Contents only).

Bonds: A Method For Preparation of DNA Microarrays, *Analytical Biochemistry*, 266(1):23–30.

* cited by examiner a) Chess-board; b) Honeycomb

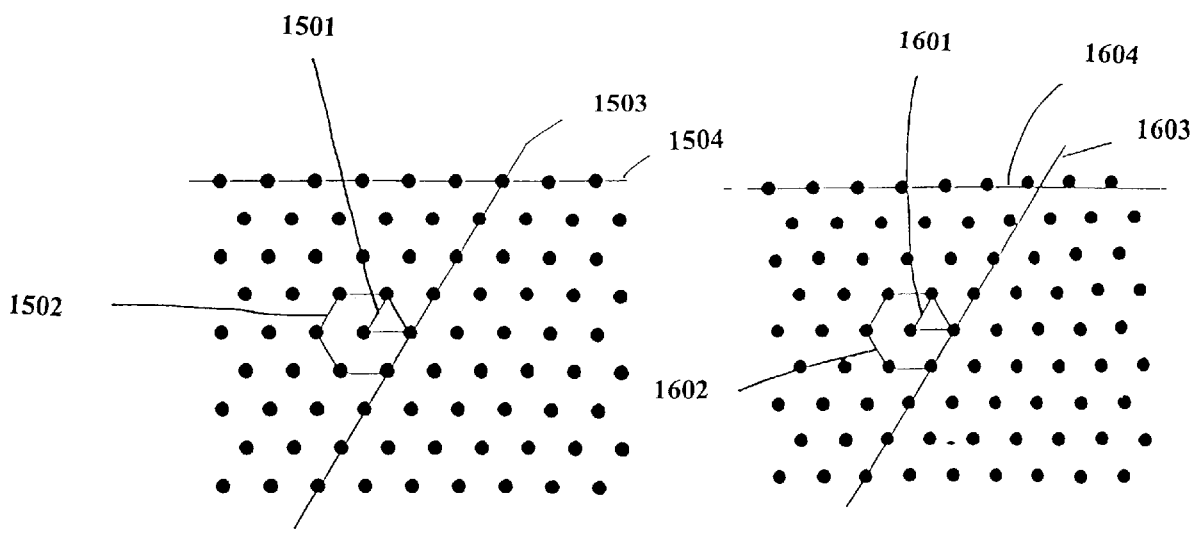
Figure 15 A highly organized matrix with orderly local and global patterns
Figure 16 A tightly packed spot array with orderly local pattern but distorting starts to appear in global pattern

MICROARRAY FABRICATION TECHNIQUES AND APPARATUS

This invention claims the benefit of priority to U.S. Provisional Application No. 60/183,737, filed on Feb. 22, 2000; No. 60/188,872, filed on Mar. 13, 2000; No. 60/216,265, filed on Jul. 6, 2000; No. 60/220,085, filed on Jul. 21, 2000; No. 60/244,711, filed on Oct. 30, 2000. This invention is also related to, titled MICROARRAY FABRICATION TECHNIQUES AND APPARATUS by inventors Shiping Chen, Yuling Luo, and Anthony C. Chen, filed on even date herewith. All of the above applications are incorporated by reference herein in their entireties as if fully set forth below.

FIELD OF THE INVENTION

The invention relates to mechanisms and methods used to form a microarray of multiple probes used to detect the presence of a target biological material or a target chemical.

BACKGROUND

A microarray is an array of spots of biological or chemical samples ("probes") immobilized at predefined positions on a substrate. Each spot contains a number of molecules of a single biological or chemical material. To interrogate the array, the microarray is flooded with a fluid containing one or more biological or chemical samples (the "target"), elements of which typically interact with one or more complementary probes on the microarray. In DNA microarrays in particular, the probes are oligonucleotide or cDNA strains, and the target is a fluorescent or radioactive-labeled DNA sample. The molecular strands in the target hybridize with complementary strands in the probe microarray. The hybridized microarray is inspected by a microarray reader, which detects the presence of the radioactive labels or which stimulates the fluorescent labels to emit light through excitation with a laser or other energy sources. The reader detects the position and strength of the label emission in the microarray. Since the probes are placed in predetermined and thus known positions in the microarray, the presence and quantity of target sequences in the fluid are identified by the position at which fluorescence or radiation is detected and the strength of the fluorescence or radiation.

Microarray technology provides an extremely useful tool to conduct biological or chemical experiments in a massive parallel fashion because of the large number of different probes that one can fabricate onto the microarray. It is particularly powerful in screening, profiling and identifying DNA samples.

Microarrays today come as two-dimensional probe matrices fabricated on solid glass or nylon substrates. Because the target samples are generally hard to produce or very expensive, it is highly desirable to perform assays on as many features as possible on a single microarray. This calls for a significant increase in probe density and quantity on a single substrate. In general, microarrays with probe pitch smaller than 500 $\mu$m (i.e. density larger than 400 probes per sqr. centimeter) is referred as high density microarrays, otherwise, they are "low density" microarrays.

There are two microarray fabrication techniques on the market, photolithographic and robotic spotting techniques. The photolithographic technique [U.S. Pat. Nos. 5,445,934, 5,744,305] adapts the same fabrication process for electronic integrated circuits to synthesize probes in situ base by base. This technique requires a large capital outlay for equipment running up to hundreds of millions of dollars. The initial setup of new microarray designs is also very expensive due to the high cost of producing photo masks. This technique is therefore only viable in mass production of standard microarrays at a very high volume. Even at high volumes, the complexity in synthesis still limits the production throughput resulting in a high microarray cost. This complexity also limits the length of the synthesized DNA strain to the level of a short oligonucleotide (~25 bases), which reduces the specificity and sensitivity of hybridization in some applications.

The established robotic spotting technique [U.S. Pat. No. 5,807,522] uses a specially designed mechanical robot, which produces a probe spot on the microarray by dipping a pin head into a fluid containing an off-line synthesized DNA and then spotting it onto the slide at a predetermined position. Washing and drying of the pins are required prior to the spotting of a different probe in the microarray. In current designs of such robotic systems, the spotting pin, and/or the stage carrying the microarray substrates move along the XYZ axes in coordination to deposit samples at controlled positions of the substrates. Because a microarray contains a very large number of different probes, this technique, although highly flexible, is inherently very slow. Even though the speed can be enhanced by employing multiple pin-heads and spotting multiple slides before washing, production throughput remains very low. This technique is therefore not suitable for high volume mass production of microarrays.

In addition to the established quill-pin spotting technologies, there are a number of microarray fabrication techniques that are being developed. These include the inkjet technology and capillary spotting.

Inkjet technology is being deployed to deposit either cDNA/oligonucleotides, or individual nucleotides at defined positions on a substrate to produce an oligonucleotide microarray through in situ synthesis. Consequently, an oligonucleotide is produced in situ one base at a time by delivering monomer-containing solutions onto selected locations, reacting the monomer, rinsing the substrate to remove excess monomers, and drying the substrate to prepare it for the next spot of monomer reactant.

An emerging spotting technique uses capillaries instead of pins to spot DNA probes onto the support. Four references discuss capillary-based spotting techniques for array fabrication:

WO 98/29736, "Multiplexed molecular analysis apparatus and method", by Genometrix Inc.

WO 00/01859, "Gene pen devices for array printing", by Orchid Biocomputer Inc.

WO 00/13796, "Capillary printing system", by Incyte Pharmaceuticals Inc.

WO 99/55461, "Redrawn capillary imaging reservoir", by Corning Inc.

In summary, due to the high cost of production, microarrays fabricated with existing technologies are far too expensive as a single use lab supply.

SUMMARY OF THE INVENTION

The invention provides a probe printing system having a print head composed of one or more bundles of randomly bundled or discretely bundled capillaries as described herein. A bundle of capillaries has a portion where at least the proximal ends of the capillaries are immobilized in a planar matrix and a facet is formed for printing. The immobilized portion is preferably sufficiently rigid that it may be used to print a probe microarray upon a substrate with minimal or no deformation (deformation may result in portions of the microarray not being printed to the substrate). The immobilized portion is therefore sufficiently rigid to ensure good contact with the substrate across the portion of the facet in contact with the substrate. The distal ends of the capillaries may be free or may be attached to reservoirs. The capillaries include, but are not limited to, fiber optic or other light-conducting capillaries, through which light as well as fluid can be conveyed; and other flexible or rigid capillaries.

A capillary bundle in one embodiment of the invention has a plurality of individual capillaries having proximal and distal ends. The outer diameter of a capillary is typically less than about 300 micron, preferably the outer diameter is less than about 100 micron. Each of the capillaries of the bundle has a channel extending from the proximal end to the distal end of the capillary, and each of the capillaries has a channel-facing wall. The channel diameter is preferably less than 100 micron.

A bundle of individual capillaries is distinguished from a unitary structure in which tubular preforms are fused to one another to form a large array of preforms and then stretched to form a unitary array of channels.

The proximal ends of capillaries of a bundle may be secured to one another in a solid mass such that the proximal ends of the capillaries are substantially coplanar at a facet of the solid mass. Proximal ends are substantially coplanar when liquid flowing through the capillaries form spots on a flat surface of the substrate when the facet of the solid mass is either pressed against the surface or is in sufficient proximity to the surface that droplets from the capillaries are deposited on the surface. Generally, proximal ends are substantially coplanar when all ends terminate within about 100 microns of one another. Preferably, proximal ends terminate within about 50 microns of one another. More preferably, proximal ends terminate within about 20 microns of one another. Even more preferably, proximal ends terminate within 5 microns of one another.

A capillary bundle may contain any number of capillaries. Preferably, the bundle contains at least about 1000, 5000, 10,000, 50,000, 100,000, or 500,000 capillaries. A capillary bundle also preferably contains at least about 83, 416, 500, 833, 1000, 4166, 5,000, 8333, 41,666, 10,000, 20,000, or 40,000 capillaries per $cm^2$ that print non-overlapping spots on a substrate.

Capillaries of the bundle may individually have a well formed at their distal ends. Such wells may be formed by etching the proximal end of a silica capillary that has a region near the channel of the capillary that is doped compared to the region nearer the outer wall. The facet of the solid mass may be coated with an electrically-conductive material to facilitate establishing a potential difference that moves probe molecules. Each of the capillaries may have a substantially uniform inner diameter from their distal ends to their proximal ends, and each of the capillaries preferably has substantially the same diameter. This assures a uniform flow rate of fluid through the capillaries, so that spot sizes are approximately equal and so that individual spots do not join together and mix. Preferably, the diameter along a capillary has no more than about 10%, more preferably no more than about 3% variation, and preferably the diameters of all of the capillaries are within about 10%, more preferably about 3% of the mean diameter of the capillaries.

The invention also provides methods of making capillary bundles, methods of correlating the myriad number of individual capillaries of a print head to the reservoirs to which they are attached, and methods of printing microarrays using any of the printing systems, capillaries, and print heads further described herein.

A capillary bundle may be formed by a number of different methods. In one method, individual capillaries are gathered together in no particular order and secured to one another to form a random bundle. In such a random bundle, the distal ends of the capillaries are grouped in a first arrangement, the proximal ends of the capillaries are grouped in a second arrangement, and the first arrangement is not identical to the second arrangement. Often, it is not possible to know which distal end corresponds to which proximal end in such a random bundle until the proximal ends and the distal ends are registered to one another.

The proximal and distal ends of the capillaries may be registered to one another using any of a number of methods. If the capillaries are light-conducting capillaries, light may be launched into a distal end of each capillary and the position of light exiting the proximal end of the capillary is noted and recorded. Other methods include registering the position using a temperature change induced by an air or another fluid flowing through the capillary or by visually observing e.g. an ink that passes through the capillary.

In another method, individual capillaries are secured to one another to form an ordered bundle. In an ordered bundle, the correlation between distal ends and proximal ends is known at the time the ordered bundle is made. No registration of distal and proximal ends is necessary. In one method of making an ordered bundle, individual capillaries are inserted into a guide plate or a set of guide plates, and the capillaries at or near the proximal and/or distal ends or over most or all of the capillaries' lengths are bonded together in a solid mass using, e.g., epoxy. The ends or capillaries may optionally be fused to form the solid mass. The guide plate or plates may be removed, since a sufficient portion of the capillaries are bonded or fused together in a solid mass at the point that the guide plates are removed. Removal of the guide plate forms a facet of the solid mass.

A print head of the invention has a capillary bundle as described herein attached or secured to a frame that is adapted to hold the capillary bundle in a print system. A print head may alternatively have a frame that holds a plurality of capillary bundles.

A print system has a print head and a plurality of reservoirs (such as those contained in a microtiter plate) in fluid communication with distal ends of the capillary bundle of the print head. A print system may have a voltage source connected to an electrically-conductive material on a facet of the print head and to an electrically conductive material contacting the probe-containing liquid near the proximal ends of the capillaries. A voltage regulator may be used to regulate the voltage and thus the rate of deposition of probe molecules.

Another print system of the invention may have a print head, a plurality of reservoirs, and a magnetic field generator that is positioned sufficiently closely to the print head to move a magnetic probe-containing fluid (such as a fluid containing magnetic beads or paramagnetic beads having probes attached to their surfaces) through the capillaries of the bundle.

A print system may have a flexible mount on which the substrate, the print head, or both are mounted. A flexible mount permits the substrate and/or print head to move and align themselves to one another to provide for improved print quality.

The print head of a print system may be configured so that it moves in only one direction (toward and away from the substrate on which probes are to be printed, or in the z-direction of an x-y-z coordinate system), with the substrates moving beneath the print head. Alternatively, the print head may be configured to move in all directions or to be stationary, with substrates being moved to the print head.

The reservoirs of a print system of the invention preferably reside in fixed positions, whereas the print head of the print system is free to move. Consequently, the capillaries of the capillary bundle of the print system have sufficient flexibility to allow capillary movement without requiring the reservoirs to also move. In addition, the reservoirs of a print system of the invention preferably reside in a regulated pressure chamber, wherein change of pressure moves solution in or out of the capillaries.

The invention provides a probe microarray comprising an arrangement of non-identical probes on a substrate in a honeycomb pattern, wherein, at the same center-to-center pitch, the density of probes is higher than that in a chessboard pattern. By "honeycomb" is meant a pattern of regular triangles and regular hexagons wherein each spot is at the center of a regular hexagon formed by six neighboring spots of equal distance to the center. The substrate may be porous or nonporous.

The invention further provides a probe microarray comprising a random arrangement of non-identical probes on a substrate. A random arrangement of non-identical probes is one in which probes on a substrate may appear to be organized locally into columns and rows or in a honeycomb pattern, but the probes do not have column and row order or honeycomb pattern across the entire microarray as is found in an array that is fabricated on a substrate using photolithographic techniques or robotic spotting techniques. Further, the individual probes of a first probe microarray having a random arrangement of non-identical probes printed using a first random bundle of capillaries will have positions on the substrate that differ from the positions of the same individual probes of a second probe microarray printed using a second random bundle of capillaries. The spatial positions of the individual probes are determined by the order and spatial relationship of the individual capillaries of the random bundle, and the order and spatial relationship of the individual capillaries in the bundle are random. A probe microarray printed using a random bundle is one example of a probe microarray made by placing non-identical probes on a substrate in a random pattern.

The probes are printed on print surface of the substrate, and the number of probes per unit area of the print surface is the print density. The print surface is that area of the substrate on which the individual probes are printed, plus the surface area between the individual probes. If there are two or more groupings of a substantial number of probes on surface of the substrate separated by surface area in which few or no probes are printed, the print surface includes the surface area between probes of a group but not the surface area of the substrate between groupings. Preferably, the print density is high so that a large number of probes can fit on a substrate. Preferably, the print density is at least about 200, 500, 1,000, 5,000, 10,000, 20,000, or 40,000 probes per $cm^2$.

The probes of the probe microarray may be oligonucleotides (the term "oligonucleotides" as used herein also includes polynucleotides, especially polynucleotides having more than about 40 bases), or the probes may be proteins, cells, or chemical compounds. A microarray may contain any number of probes, and preferably the number of probes in the microarray is at least about 1,000, 5,000, 10,000, 50,000, 100,000, or 500,000. A probe microarray may be formed by attaching any of the probes discussed above individually to beads, which beads are affixed to the substrate: covalently; non-covalently through e.g. ionic, polar, or Van der Waals forces or conformational interaction of binding moieties attached to the beads and substrate (such as biotin-avidin or biotin-streptavidin); magnetically; or any other method for attaching beads to a substrate.

One method of the invention forms a probe microarray on a substrate. This method comprises the acts of: providing a print head having a bundle of individual capillaries; passing non-identical probe-containing liquids through a number of the capillaries simultaneously; and printing the non-identical probe-containing liquids onto the substrate to form the probe microarray. The probe-containing liquids may contain the probes in a suitable liquid carrier, or the probe-containing liquids may contain probes attached to e.g. beads such as magnetic beads that are deposited onto the substrate using a magnetic field to move the beads through the capillaries.

The individual capillaries of the bundle may be light-conducting capillaries. For instance, a light-conducting capillary is formed of a transparent material and has a properly designed refractive index profile across its cross section so that the capillary transports light from the distal end to the proximal end of the capillary. The capillary can therefore conduct light and fluid individually or simultaneously.

In one embodiment of the invention, a light-conducting capillary has a first portion having a first refractive index and a second portion having a second refractive index whose value is greater than the first refractive index wherein said second portion is inside the first portion. The light-conducting capillary further has a proximal end, a distal end, an axis, an inner wall defining a channel through the capillary, and an outer wall. The inner wall extends coaxially with the axis of the capillary, and the outer wall also extends coaxially with the axis of the capillary. The first portion and the second portion are configured such that a light beam launched into the proximal end is transmitted along the capillary and exits the capillary at the distal end. The channel of the capillary has a cross-sectional area that is sufficiently large that a fluid entering the channel at the proximal end of the capillary discharges at the distal end of the capillary. In one instance, a light-conducting capillary is formed by selecting a liquid carrier which has a refractive index that is sufficiently high compared to the refractive index of the capillary that the liquid acts as a light-conductive core and the capillary acts as cladding. Preferably, a light-conducting capillary is an optical fiber capillary, in which the capillary itself is configured to be light-conducting by providing a region of high refractive index along the length of the capillary that is bounded by regions of lower refractive index. The optical fiber capillary may be formed of doped silica, for instance. The cross-sectional area and outer diameter of the capillary is such that at least about 1000, 10,000, 100,000, or 500,000 non-overlapping spots of liquid may be deposited in an area of 12 $cm^2$ on a substrate by bundling capillaries together. A bundle of light-conducting capillaries may be formed, and the bundle may be utilized as part of a print-head or printing system as described herein.

A capillary as used in a print head of the invention typically has a large ratio of length to outer diameter. The length of a capillary can be at least about 20 cm, and preferably at least about 100 cm. A capillary as used in the invention typically has an outer diameter less than 200 micron and preferably less than 100 micron. Consequently, the ratio of length to outer diameter ranges can be the ratio of any of these values, and typically the ratio of length to outer diameter is greater than 500, 4000, 10,000, or 30,000.

Thus, this invention features a unique carrier that simultaneously conduct light and transport minute quantity of material. The light can be used to carry information and/or energy. Individual carriers may be used as medical devices (e.g., for observing and treating diseased tissues or organs) or industrial devices (e.g., for inspecting and treating cracks or leaks). A plurality of a carrier can be bundled together to provide massive parallel capability in handling multiple samples and multiple information channels.

Light may be conducted through light-conducting capillaries of a print head before depositing probes or during probe deposition to e.g. prepare a light-sensitive area to receive the probes. Light may be conducted through the light-conducting capillaries of a print head during probe deposition to measure the distance between the capillary facet and the substrate and to detect in real time whether the probe fluid contacts the substrate surface. Light may be conducted through the capillaries after depositing probes as a quality control measure to determine if probes have been deposited, especially where some of the molecules of each probe incorporate a tag that fluoresces when illuminated with light of the appropriate wavelength. Preferably, the facet of the print head used to print the random probe microarray has at least about 83, 416, 833, 4166, 8333, or 41,666 capillaries per square centimeter. An electric potential may optionally be applied across the capillaries to move the probes in the probe-containing liquids through the capillaries. A probe microarray of the invention can be formed using any of the methods specified above.

A probe microarray of this invention may also comprise a substrate that is coated with a layer of light sensitive material, and a plurality of probes (i.e. spots of probe molecules) on a surface of the substrate. A light sensitive material may be hydrophobic but turn hydrophilic upon exposure to light of the appropriate wavelength. Probes can be more easily positioned on a portion of the substrate that is hydrophilic if the liquid in which probe molecules are carried is polar (e.g. water).

The invention also provides a method of using the probe microarrays discussed herein. The method includes contacting a probe microarray with a liquid which contains target components for a sufficient period of time to allow target components in the liquid to associate with complementary probes of the probe microarray, if any, to form target-probe complexes, and determining the positions of the target-probe complexes in the microarray. The positions may be correlated with a probe identity or with a target identity using, e.g., a software file or dedicated memory such as read-only memory that contains data on the probe and/or target identities as a function of probe position on the substrate.

In addition, the invention provides systems and methods of printing microarrays, even when the substrate and print head are not perfectly aligned and would otherwise not print a complete microarray of probes that the print head is capable of printing.

The invention further provides quality control instruments and methods for inspecting microarrays after their formation.

In one method of detecting the unintentional absence of probes from a probe microarray or the unintentional overlapping of adjacent probes, or mis-sizing of probe spots on the array, the method comprises positioning a microarray beneath a light detector and shining light on a probe-containing surface of the microarray at an angle to the microarray. The angle is sufficient to reflect light from the probe-containing surface in a first area of the surface that contains no probes. The angle is also sufficient to scatter light to the detector in a second area of the surface that contains probes. A light pattern array formed by scattering the light to the detector is detected, and the light pattern array is compared to an expected pattern array to determine if the light pattern array matches the expected pattern array.

In another method of detecting the unintentional absence of probes from a probe microarray or the unintentional overlapping of adjacent probes, or the mis-sizing of probe spots on the array, the method comprises positioning a microarray beneath a light detector and shining light on a surface of the microarray at an angle sufficient to cause total internal reflection of the light within the microarray. A light pattern array is formed by detecting the light refracting from within the microarray at a probe-containing area of the microarray and comparing the light pattern array to an expected pattern array to determine if the light pattern array matches the expected pattern array.

The invention also provides quality control instruments. One instrument detects the unintentional absence of probes from a probe microarray or the unintentional overlapping of adjacent probes, or the mis-sizing of probe spots on the array. This quality control instrument has a light detector and a light source configured to shine light onto a probe-containing surface of the microarray at a first angle to the microarray. The light contacting a first set of areas of the probe-containing surface that contain no probes reflects away from the light detector. The light contacting a second set of probe-containing areas of the probe-containing surface is scattered sufficiently that the detector detects the presence of the light at the second set of areas. A microprocessor receives data signals from the light detector, which data signals correspond to a light pattern array formed by the light scattered from said probe-containing areas of the microarray. The microprocessor is configured to compare the data signals corresponding to the light pattern array to data corresponding to an expected pattern array to determine if the light pattern array matches the expected pattern array.

Another quality control instrument of the invention also detects the unintentional absence of probes from a probe microarray or the unintentional overlapping of adjacent probes, or the mis-sizing of probe spots on the array. This quality control instrument has a light detector and a light source configured to shine light onto a surface of a microarray placed beneath the light detector. The light shines at an angle sufficient to cause total internal reflection of the light within the microarray. A microprocessor receives data signals from the light detector, which data signals correspond to a light pattern array formed by the light refracting from within the microarray at probe-containing areas of the microarray. The microprocessor is configured to compare the data signals corresponding to the light pattern array to data corresponding to an expected pattern array to determine if the light pattern array matches the expected pattern array.

A preferred arrayer based on the invention is simple and low cost and capable of producing one high-density (down to 10 $\mu$m probe pitch), large scale (500,000 or more probes per slide) microarray in a single stamping action. The production throughput for a single arrayer can be as high as 5, 10 or 20 slides per second. Such a throughput gives it advantage in production of high volume and standard microarray products. In addition, it has great flexibility for custom microarrays as the entire or part of the capillaries in the stamp can be quickly washed clean and reused for different probe samples.

The invention thus provides a number of systems, components, means, and methods for producing probe microarrays as are more fully described below. This Summary section of the disclosure provides a summary of some salient points of the invention, but this section is not to be interpreted as limiting the scope of the invention to only those features and embodiments discussed in this section. Instead, the invention involves all components, systems, and methods discussed in this and the following sections in addition to those defined by the appended claims.

BRIEF DESCRIPTION OF THE DRAWINGS

FIG. 15 illustrates a honeycomb pattern of probes that can be formed by a print head made using a guide plate having holes in a honeycomb pattern.

FIG. 16 illustrates a random pattern of probes which can form when printed using a random-bundle print head.

DETAILED DESCRIPTION OF THE INVENTION

In the description below, a DNA microarray is used as one embodiment of the invention. The techniques described herein can also be used to produce microarrays of a wide range of biological and chemical probe materials which include but are not limited to deoxyribonucleic acids (DNA), ribonucleic acids (RNA), synthetic oligonucleotides, antibodies, cells, tissue, proteins, peptides, lectins, modified polysaccharides, synthetic composite macromolecules, functionalized nanostructures, synthetic polymers, modified/blocked nucleotides/nucleosides, modified/blocked amino acids, fluorophores, chromophores, ligands, chelates, haptens, drug compounds, and chemical compounds that have associated substance which binds, associates, or interacts with the probe material. The samples being deposited on the microarray substrate using the technology disclosed herein can take or be carried by any physical form that can be transported through a capillary. These include but are not limited to aqueous or non-aqueous fluid, gel, paste, bead, powder and particles suspended in aqueous or non-aqueous liquid.

The substrate may be formed of any material on which the probes can be deposited. The substrate itself may be capable of immobilizing the particular probes used, or the substrate may be capable of modification (for example, by coating) so that it is capable of such immobilization. The substrate may be porous or nonporous materials. Preferred materials for the substrate of the present invention include silica, glass, metals, plastics, and polymers.

For immobilizing polynucleotides and polypeptides, glass is a preferred material because polynucleotides and polypeptides can be covalently attached to a treated glass surface and glass gives out minimal fluorescent noise signal. The glass may be layered on another material, or it may be core or base material of the apparatus, or both. Another example of a substrate includes a plastic or polymer tape as a base substrate, with a coating of silica for probe embodiment. In this embodiment, a further layer of metallic material may be added, either on the opposite side of the tape from the silica layer, or sandwiched between the silica layer and the polymer or plastic.

Figure 1:
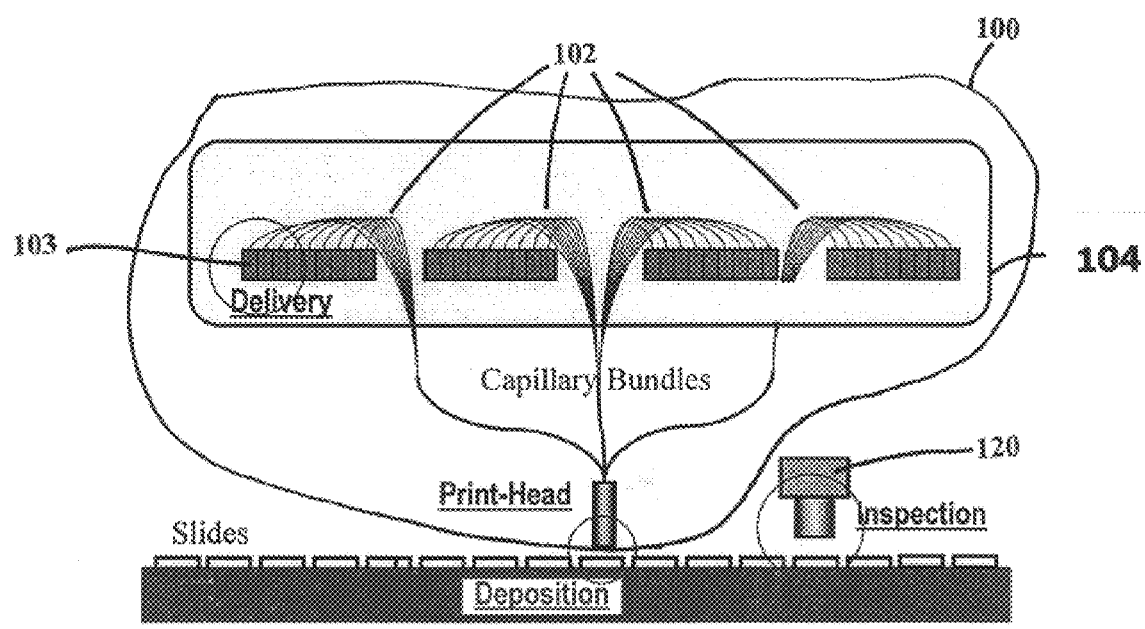
FIG. 1 is a schematic diagram of one embodiment of a microarray fabrication system.

A microarray fabrication system based on this invention is illustrated schematically in FIG. 1. The heart of the system 100 is a print-head 101 comprising a large number of flexible capillaries 102. Each capillary in the print-head is fluidly linked to a reservoir 103 containing a specific DNA sample. The reservoirs may take the form of fluid wells in standard microtiter plates 104. Probes are delivered to the print-head via the capillaries and the entire set of probes can be deposited on to the substrate 110 in a single printing action. There is an inspection system 120 to inspect the quality of the fabricated microarrays online or off-line.

In the invented system shown in FIG. 1, multiple microarray substrates are carried on a translation stage, which moves in a single axis in a stepping fashion to align a blank substrate under the print head. The translation stage can be a rotation stage or a conveyor belt based system equipped with substrate loading and unloading stations. In this way, blank substrates can be fed to a print position beneath the print head in a continuous fashion. The print head can deposit an entire set of probes by moving only a very short distance (<1 mm) in one axis (up and down in the z axis). Or the print head may not have to move at all if electric or magnetic induced deposition methods are used, which are described below. As a result, microarray manufacturing can be carried out in a continuous fashion at a very high throughput.

In robotic pin deposition methods and other deposition methods in which probes may be placed on a substrate, the print head moves in the x and y axes as well as the z axis. The pins travel a long distance, in the order of a meter, and thus such conventional deposition methods require a substantial period of time to fabricate an array on a substrate. A print system of the invention can thus be configured to travel a short distance and require little time to print a microarray.

The probe reservoirs in the system can be positioned above the print head and substrates, as shown in FIG. 1. The print head deposits the probe down to the upper surface of the substrate. The advantage of such an arrangement is that, after priming, the fluid flow inside the capillaries can be driven by the gravity, which is very stable and uniform among capillaries and can be precisely controlled by adjusting the height of the reservoirs. An alternative arrangement is to place the reservoirs below the print head. The print head moves up to deposit probes on substrates, which are held "face-down" on the stage. In this configuration, the capillaries are short and relatively straight. The probe-containing fluid can be moved to the substrate by pressurizing the reservoirs, for instance.

The basic elements of the technology of this invention include methods and apparatus for print-head, fluid delivery, probe deposition and inspection. The details of these technological elements are discussed in the following sections.

1. Print-Head

The print-head receives probe fluids from their individual reservoirs and deposits them in small volumes onto the microarray substrate at each printing action. A print-head is a solidified piece of e.g. polymer such as a thermo-setting or other polymer (for example, an epoxy polymer) that surrounds the proximal ends of the capillaries, and its facet or face that contacts the substrate is fabricated to conform to the surface contour of the microarray substrate in order to facilitate uniformed probe deposition.

Figure 2:
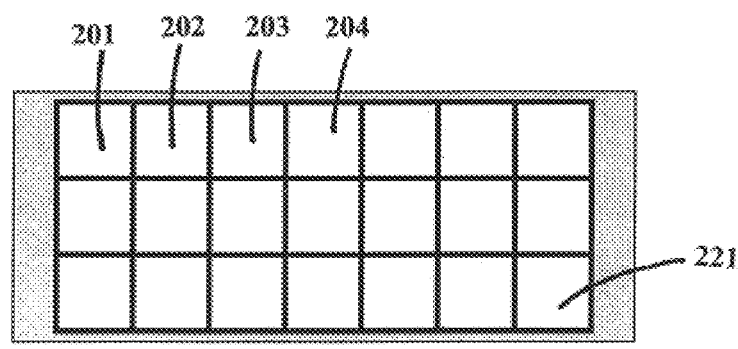
FIG. 2 illustrates a print-head containing the immobilized portion of twenty-one capillary bundles.

The print-head is solid or has sufficient flexibility to conform to the substrate surface on which a micro-array is to be printed. The print-head 200 may contain a single capillary bundle or, as shown in FIG. 2, multiple capillary bundles 201, 202, 203, 204, . . . , 221. In the multiple bundle configuration, it is preferred that the outline shape of each bundle is rectangular or square so that the capillary bundles can easily be assembled to form a structured matrix in a rectangular print-head 200 (although other shapes are possible). In this way, 1) the print head can be configured to print on most or all of the surface area of a standard microscope slide; 2) the position and orientation of each bundle in the system is known; and 3) it is easier to identify each capillary in a bundle. Alternatively, the outline shape of each bundle could be round or in other shapes.

Capillaries used in the system can be made of silica or other suitable materials such as glass, ceramics, polymer or metal. The capillaries conduct the probes of interest from the distal ends of the capillaries to the proximal ends of the capillaries, and thus capillaries that are bundled to form a print head are manufactured from a material that does not remove a substantial number of probe molecules from their carrier liquid and attach the molecules to the walls or to another material positioned within the capillaries.

The capillary bundle is assembled from a large number of individual, ready-made capillaries. Capillaries are bundled together, solidified into a single mass or block at their proximal ends using an adhesive or by fusing the capillary walls at the proximal ends of the capillaries together, and eventually assembled into the print-head while the distal ends of capillaries are left loose or attached to reservoirs or a plate that dips into a set of reservoirs.

The proximal ends of the capillaries may be solidified together using a cement or epoxy that forms a rigid block, or the proximal ends may be solidified together using a polymer that is somewhat flexible, so that the surface conforms to the substrate when pressed against it to provide better printing in the event that the printing face or facet of the block is not perfectly parallel to the surface of the substrate to be printed. The printing face may optionally be polished to provide a very flat surface, so that the proximal ends of the capillaries terminate within 100 micron of each other, for instance. That is, if the printing face is held above and parallel to a plane and separated by a nominal distance z, the difference between the shortest distance that a proximal end in the facet terminates from the plane and the greatest distance that a proximal end in the facet terminates from the plane is no more than about e.g. 100 micron. Preferably, the difference in termination distances is no more than about 50 micron, more preferably no more than about 20 micron, and more preferably no more than about 5 micron. The trimmed block has sufficient rigidity to assure its facet remains parallel to the substrate during printing.

In one embodiment of the invention, the solid mass contains no more than about 10 cm of the lengths of the capillaries (and thus the printhead in this embodiment is no more than about 10 cm thick), and the loose or free ends of the capillaries are from about 1 to about 3 meters in length. Consequently, the ratio of length of loose capillary to thickness of solid mass is preferably at least about 10 and more preferably at least about 30. The solid mass may be about 2 cm thick or thinner, and in this instance the ratio of length of loose capillary to thickness of solid mass is preferably at least about 50 and more preferably at least about 150. The solid mass needs only to be sufficiently thick that the print head, alone or in combination with a frame that forms part of the print system, is sufficiently rigid that the solid mass does not deform appreciably under printing conditions, so that a microarray is formed when probes are printed onto a substrate. The loose ends of the capillaries are sufficiently long to be in fluid communication with the reservoirs or with outlet pipes connected to the reservoirs. Preferably, the loose ends are also sufficiently long that the loose portions of the capillaries accommodate any up-and-down movement of the print head with little stress to the capillaries, so that the capillaries do not crack or break during use.

Figure 18:
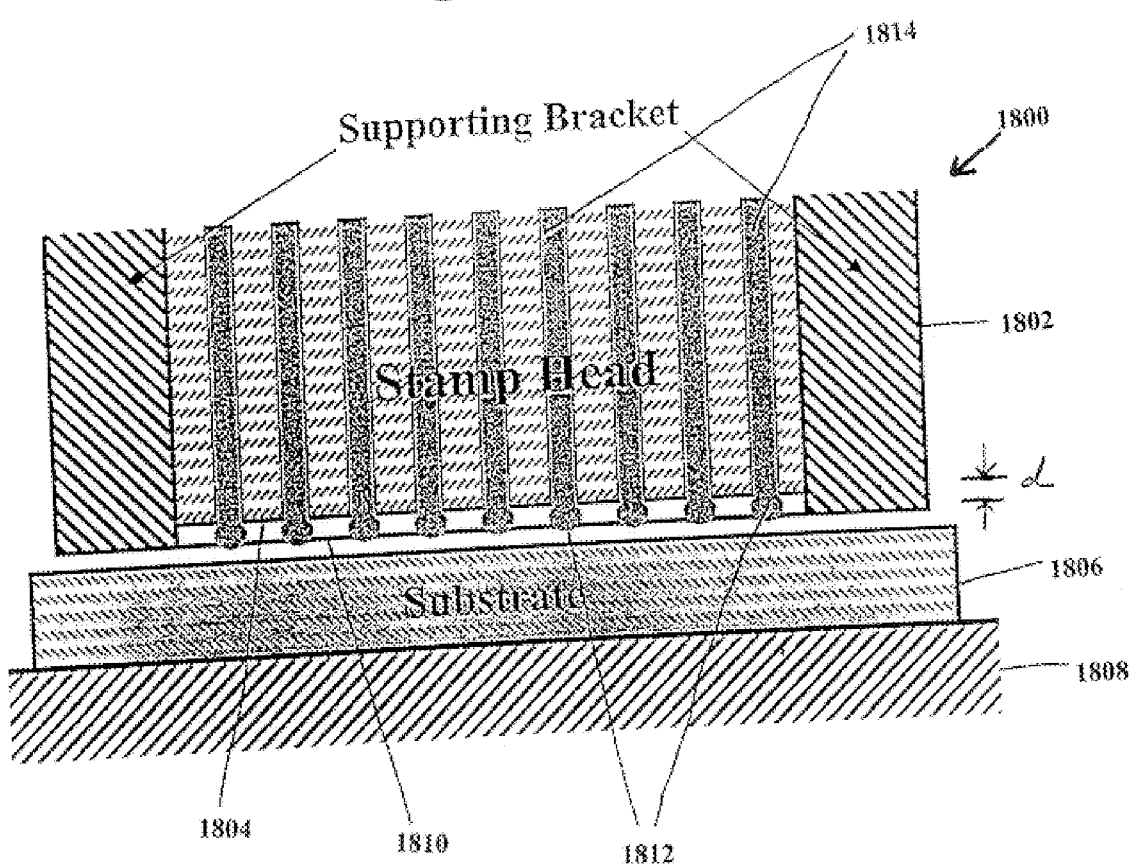
FIG. 18 illustrates a print system having a collar or support that contacts the substrate or structure around the substrate and is sufficiently long to prevent the print head from contacting the substrate. At the same time, it is not so high that it prevents droplets from the capillaries from contacting the substrate surface.

In another embodiment of the invention as illustrated in FIG. 18, the print head 1800 is equipped with a supporting bracket or collar 1802 that prevents the facet 1804 of the print head from contacting the substrate 1806 held on substrate support 1808. The facet, especially any functional coating on the surface (such as a coating of an electrically-conductive material), may be damaged after repeated contact with the substrate. Consequently, the supporting bracket helps to prolong the life of the printhead. The vertical distance d illustrated in FIG. 18 between the edge of the collar 1810 and the facet 1804 is selected so that the printhead does not contact the substrate but is still sufficiently close to deposit droplets 1812 of probe-containing fluids 1814 onto the substrate. The collar need not be a solid piece of cylindrically-shaped material as illustrated. The collar may consist of a frame that attaches to the print head and has feet or shafts that protrude to prevent the facet from contacting the substrate, for instance.

Figure 19:
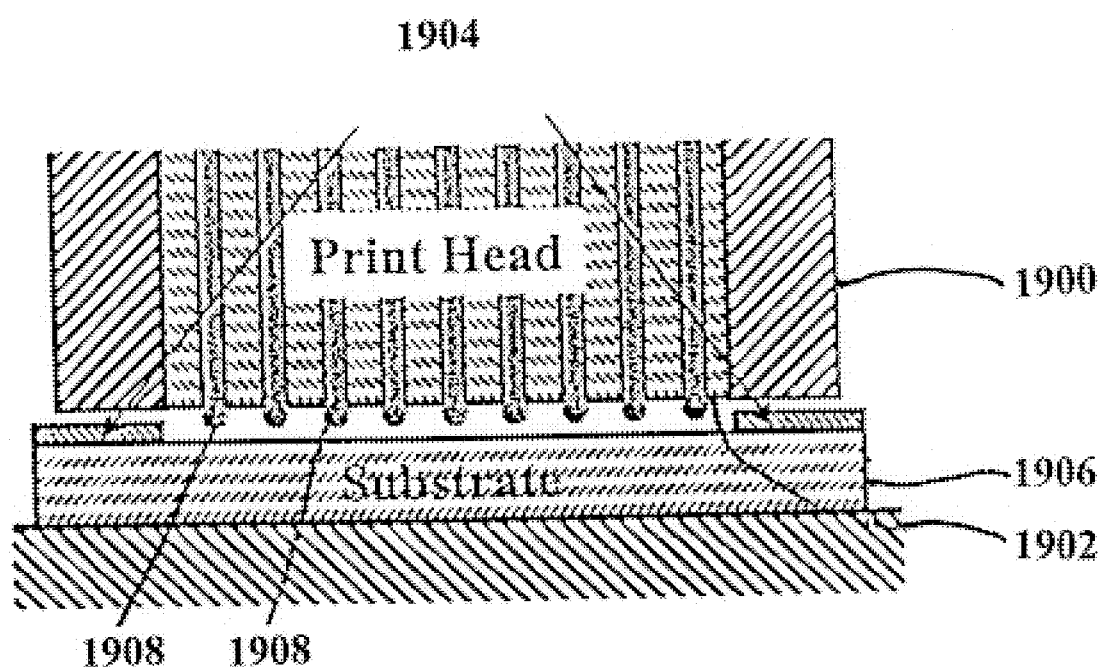
FIG. 19 illustrates an alternative printing arrangement where the facet of the print head is flat but there is a riser at the edge of, or around, the substrate that is sufficiently high to prevent the print head from directly contacting the substrate. At the same time, it is not so high that it prevents droplets from the capillaries from contacting the substrate surface.

Alternatively, as shown in FIG. 19, the facet 1902 of print head 1900 can be flat and a riser 1904 may be placed on the outer region of the substrate 1906 to prevent the printhead from contacting the substrate while still depositing droplets 1908 of probe-containing fluids. Further, this same effect can be achieved by positioning a collar of suitable dimensions around the substrate. The collar can be rigid, or alternatively the collar may contain a cushioning portion formed from a polymer or felt, for instance, upon which edges of the facet press when the facet is moved toward the substrate. The cushioning portion is positioned so that the facet does not contact the substrate, even though the cushioning material is compressed and the print head is printing the microarray on the substrate. The cushioning portion provides a "softer" portion upon which the facet lands, helping to prevent the facet from being damaged.

Figure 3:
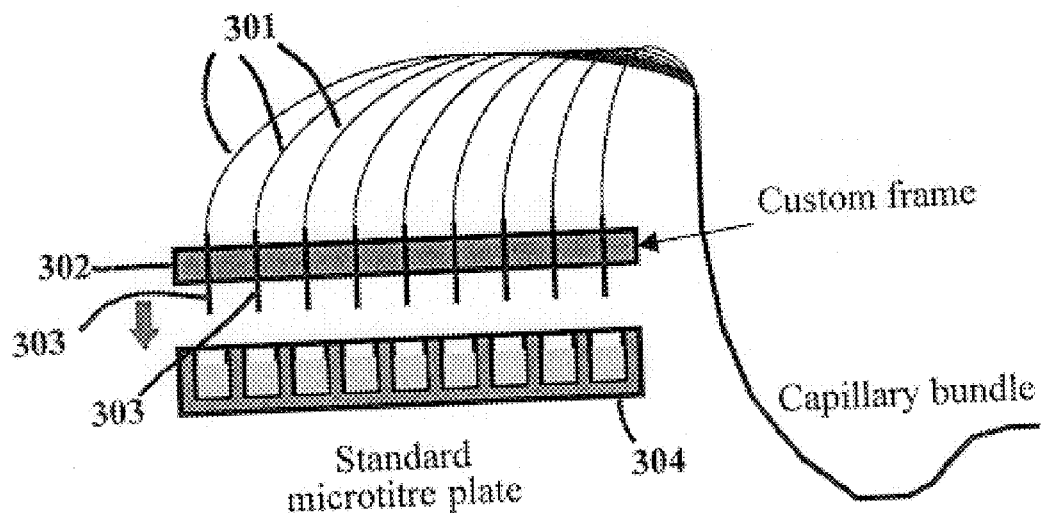
FIG. 3 illustrates a random capillary bundle linked to a frame that has suction portions that dip into the wells of a standard microtiter plate.

Each capillary can be fluidly linked to a probe reservoir, which may be the well in a standard microtiter plate. The linkage can be made permanent by gluing the capillary to a hole at the bottom of a microplate well. Alternatively, as shown in FIG. 3, the capillaries 301 can be permanently fixed to a frame 302, which holds the positions of capillary tips 303 in a grid, which has the same spatial pattern and pitch as a standard microplate 304. Then the frame can be locked on to a standard microplate to establish the fluid linkage for each capillary. In this way, the microplate after fabrication can be taken off the arrayer for long-term storage. It is also possible to wash the capillaries after the fabrication of a particular microarray, then install a new set of microplates to make a different microarray.

Following is a description of two different methods for making the assembled capillary bundle. These are the "tight-pack" and "guide-plate" methods, respectively.

1.1 Tight-Pack Method

In the tight-pack method, a large number of hair-thin, flexible capillaries are tightly packed in random order into a bundle at the proximal ends of the capillaries, in which the outer surface of a capillary is in direct contact with that of adjacent capillaries. In a tight packing of random capillaries, the capillaries take up positions in reference to each other. The local spatial pattern may be regular, e.g. the centers of every three adjacent spots may form an equilateral triangle, and six spots surrounding any spot may form a hexagon. However, minute misalignment in the random bundle of capillaries soon accumulates and results in distortion of the global alignment of the spots as illustrated in FIG. 2 and FIG. 16. As the number of spots increases, the distortion is amplified. The global spatial pattern becomes random.

However, although such a bundle may be used to print a probe microarray at high density, the microarray is useless for printing because the association between a capillary facet in the bundle and the fluid reservoir that it linked to, thus the probe identity, is lost. Capillaries randomly packed to form a capillary bundle can be made suitable for microarray printing by re-establishing the one-to-one association of each capillary between the proximal and distal end of the bundle after the bundle has been made.

Figure 4:
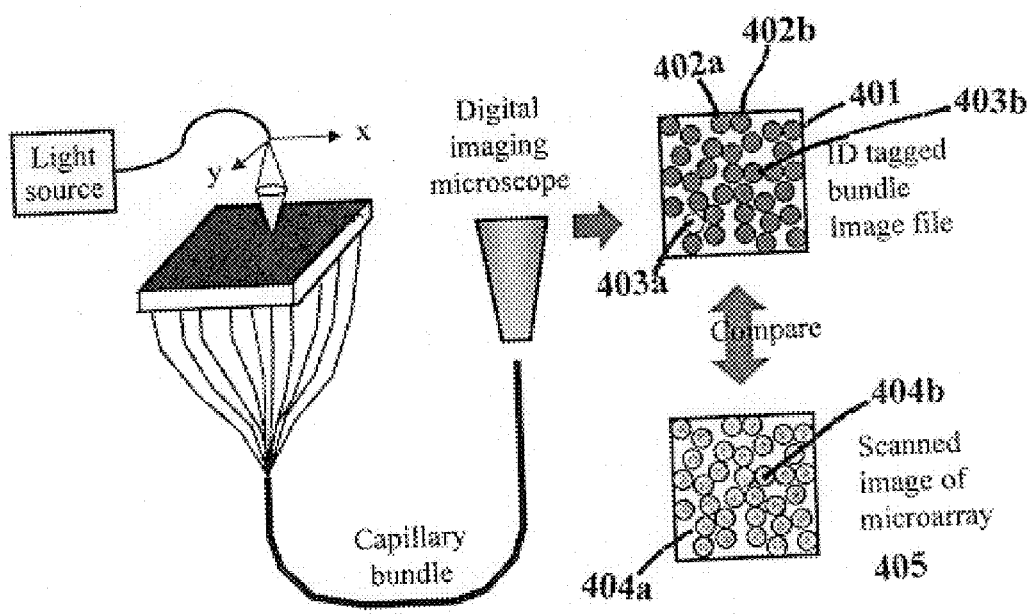
FIG. 4 illustrates equipment for and a method of using light to register the proximal and distal ends of capillaries in a random bundle.

There are a number of ways to re-establish the capillary association in a tightly packed bundle. These are:
1) Use a type of capillary that is not only capable of transporting fluid through the capillary, but is also capable of transmitting light like an optical fiber. Capillary-reservoir association can then be re-established by launching light into each capillary from the reservoir end and observing the position of the exiting light at the bundle end, using an imaging device as shown in FIG. 4. This imaging device can be either a CCD based digital microscope or a scanning microscope. Light guiding capillaries can be produced by creating an inner region in the capillary, in which the optical refractive index is higher than the outer region around it. Such a region will be able to trap the light inside it and guide the light all the way through the capillary.

This light trapping region inside capillary can be created in many different ways. A first method is to coat the outer surface of a silica capillary with a polymer with lower refractive index. A second method is to fill a silica capillary using a transparent fluid with a higher refractive index than that of the capillary to create a temporary fluid core capable of transmitting light through the capillary. A third, also preferred, method is to draw the capillary out of a preform. Such a preform can be made by following the modified chemical vapor deposition (MCVD) procedure widely used in the optical fiber industry for optical fiber perform fabrication, then drawing the preform without collapsing the central cavity at the final step. Alternatively, this preform can also be made by drilling a hole of suitable size through the axis of a multimode optical fiber preform or depositing a layer of fluoride doped silica outside a suitable pure silica tube. Since fluoride doping lowers the refractive index of pure silica, it forms a cladding to help trapping light inside the pure silica region around the central cavity.

2) Blow air into the capillaries one by one from the distal end and use a micro-flow detection device at the bundle proximal end to locate the outlet of the air flow. The position coordinate of the capillary facet is registered among other capillaries in the bundle. A micro sized hot wire or temperature probe can be used for the flow detection because the air current caused by air exiting the capillary alters the thermal balance at the probe.

3) Fill capillaries with ink from the distal end and observe where the ink exits the proximal end at the bundle facet using an imaging microscope and register its position. Capillaries can be filled one at a time or several at a time using ink of different colors.

4) Use metal capillaries insulated from one another by e.g. a dielectric such as a silica coating, or form dielectric capillaries with a metal layer and dielectric coating over the metal layer. The capillary-reservoir association can be established by placing a voltage on the distal or proximal end of the capillary and sensing the voltage on the proximal or distal end of the capillary, respectively, and determining the position of the capillary relative to the other capillaries.

The invention also provides two ways to automatically register the identity of a specific capillary in a bundle formed using any of the four methods described above. Capillary position may be registered by way of an absolute coordinate system, or capillary position may be registered to an image of the facet face.

1) Absolute Coordinates

Figure 5:
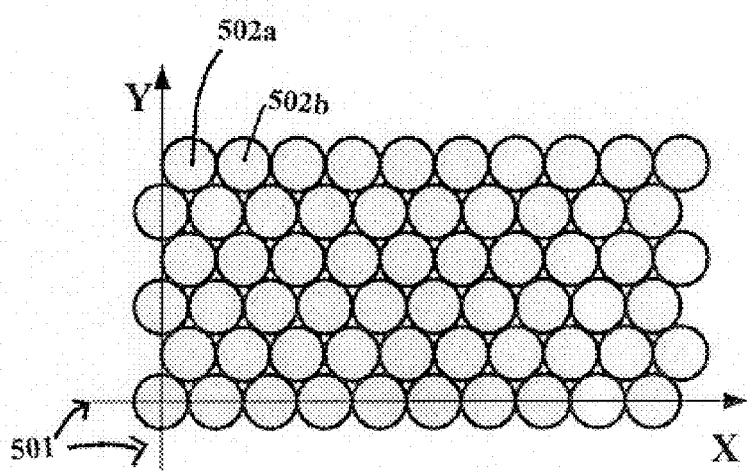
FIG. 5 illustrates one method of identifying the position of a proximal end of a capillary in the immobilized portion of the bundle.

Referring to FIG. 5, an XY coordinate system, 501 for example, can be established with reference to the edges of the bundle, and the identity of each capillary 502a, 502b, etc. can be registered by the system through its unique coordinates in the coordinate system. In this instance, the coordinates represent a mathematical vector that can be drawn from the origin of the coordinate system to the capillaries. The coordinates can be recorded in a database or otherwise saved in digital or analog form, and the coordinates can be associated with information on the position of corresponding reservoirs or distal ends to correlate or register the proximal end of each capillary with its associated reservoir or distal end. This approach is relatively easy to implement if the outline shape of the bundle is square or rectangular and the capillaries are packed tightly, so that, as shown in FIG. 5, the capillaries form a honeycomb pattern or other regular pattern. This method also tolerates at least a moderate degree of positional randomness in the bundle.

2) Image Matching

When the capillaries are completely random and there is no obvious spatial pattern in the bundle, an image matching method can be employed to register capillary identities. In this method, as illustrated in FIG. 4, a computer records data representing an image 401 of the bundle facet to a file. Each capillary in the image (e.g. 402a, 402b, ...) is correlated to its probe reservoir using e.g. one of the methods above, thereby building a database or forming other data correlating reservoirs with their corresponding capillaries. The spot pattern of the printed microarray will be a precise hard copy of the capillary facets in the bundle. Therefore DNA placed in a reservoir is printed in a known position, and this information can be correlated with the facet image to determine where probes are in the microarray. After hybridization, the microarray is scanned by a microarray scanner, which generates a pair of digital images at different fluorescent wavelengths as described in U.S. Pat. No. 5,800,992, which is incorporated by reference in its entirety herein. The scanned image can then be compared to the facet image stored in the computer to establish the DNA identity of each spot in the microarray. To make the image comparison easier, selected small number of wells in the plate can be filled with a special paint or ink or a fluid tagged with a distinctive dye. These distinctive spots 403a, 403b, on the scanned image of the probe microarray can then be used as reference points to match spots 404a, 404b on the scanned image 405 with the ID tagged image file of the capillary bundle, pre-stored in the computer.

A single bundle consisting of 100,000 or more capillaries can be fabricated and ID tagged in this way. However, it may be more beneficial to limit the number of capillaries in a random bundle to a smaller number, e.g., 1536. Then, multiple such random bundles can be assembled into an orderly bundle matrix as shown in FIG. 2 to form a print-head. This allows the utilization of standard microtiter plates with 1536 or fewer wells widely in use. Secondly, this arrangement provides greater printing flexibility. Multiple probes can be organized into different groups with one bundle per group, then mixed-and-matched to produce different microarrays for different applications. Finally, this arrangement gives the user the option and flexibility to scan only one group of probes on the microarray, wherever necessary to save time.

Considering a Particular Embodiment of the Above Described Arrangement:

Assuming capillaries with an outer diameter of 100 $\mu$m are used and each bundle is linked to a 1536-well or four 384-well microtiter plates, the capillary bundle would have a 4 mm×4 mm cross section. 75 such bundles can be easily assembled into a 5×15 orderly bundle matrix, which could produce a microarray consisting 115,200 probes in one stamp and covering a 2 cm×6 cm area on a microscope slide.

A modified form of the "tight-pack" method may also be used to form an assembled capillary bundle. Instead of tightly packing the capillaries, the capillaries may be packed more loosely. The local order as well as long-range order of the capillaries becomes random, resulting in a random array of probes in the microarray when printed.

1.2 Guide-Plate Method

Figure 6:
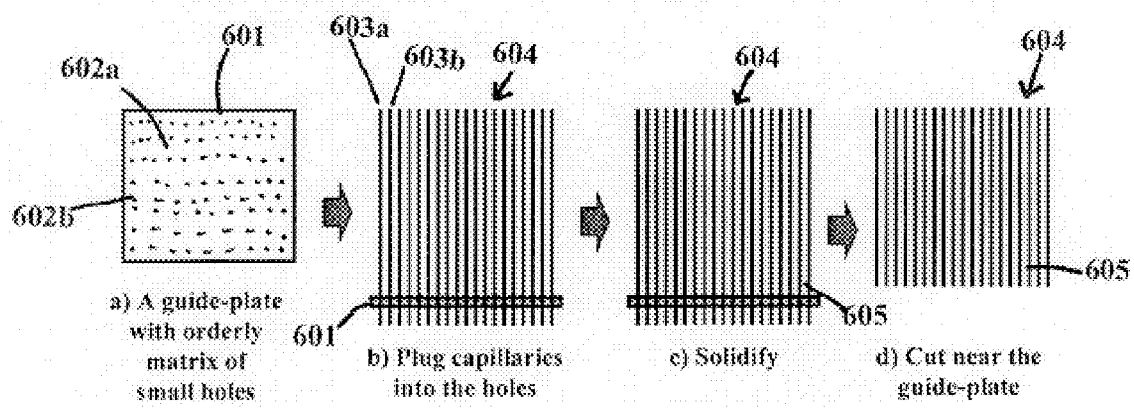
FIG. 6 illustrates steps in fabricating a capillary bundle using a guide plate that is removed to form the finished bundle.

The guide-plate method for capillary bundle fabrication is illustrated in FIG. 6. A guide-plate 601 as seen from above in FIG. 6a has an orderly matrix of small holes 602a, 602b, ... etc. fabricated through precision drilling. Alternatively, the guide plate can be made of glass and produced by slicing fused capillary array tubing drawn from a larger glass preform as described in U.S. Pat. No. 4,010,019 and 5,276,327. The plate can be made of any suitable material such as metal, glass or plastic and can also be relatively thin and/or deformable and/or fragile. The hole diameter should be slightly larger than the outer diameter of the capillaries to be used. Capillaries 603a, 603b, ... are carefully plugged into the holes to form a loose bundle 604, as illustrated in FIG. 6b. The bundle 604 is solidified at the section near the guide-plate as shown in FIG. 6c using epoxy 605, cement or other suitable solidification techniques. Finally, the solidified portion is cut at a position very close to the guide-plate, to remove the guide plate, as shown in FIG. 6d.

Because the holes are positioned in an orderly matrix at the guide-plate and the bundle is cut very close to the guide-plate, the spatial position of each capillary in the fabricated bundle will be in an orderly matrix the same as the holes in the guide-plate. Also, because the bundle is in one solid piece, it can be polished to achieve a high degree of flatness and at the same time, is mechanically robust for printing. In addition, since the capillaries are in an orderly matrix, the position of the capillary in matrix is known, and therefore the position of the capillary establishes the position of a probe in a microarray printed on a substrate. No ID tagging procedure is required.

A guide plate may be configured in any shape desired. It may be, e.g., a block, a sphere, a plate, or any other shape so long as the shape has holes or pores into which the capillaries may be inserted.

Instead of using a plate, a grid of wires or strings or strands (preferably interwoven) can be formed, and the individual capillaries can be inserted within spaces in the loose grid to form the capillary bundle. The grid can be tightened to pull the capillaries close to one another, and the proximal end, distal end, and/or intermediate portions can be adhered together using e.g. an adhesive to form a solid mass. Any strands of the grid that form part of the solid mass may be trimmed flush with the solid mass, and other free strands may be removed to provide the fiber bundle.

2. Fluid Delivery

The functions of the fluid delivery sub-system in the arrayer are to

Transport probe fluid from the reservoir to the print-head through its respective capillary;

Ensure the flow rate to be constant in each capillary and uniform across the print-head.

2.1 Fluid Transport

This invention offers several methods to drive the probe fluid from its reservoir into the capillary and towards the print-head. They can be used alone or in any combination of 2 or more in the fluid delivery sub-system. These methods include:

Air pressure A differential air (or other gas such as nitrogen) pressure can be established and maintained between the proximal and distal ends of the capillary bundles, which will translate into hydraulic pressure to drive the probe fluids.

Gravity Once the capillaries are filled with the probe fluids, a constant flow can be maintained and controlled by adjusting the vertical positions of the fluid reservoirs, e.g. the microtiter plates, with respect to the position of the print-head.

Electric field Because DNA fluids are negatively charged, a voltage applied between the reservoir and the print-head can be used to control the flow of the fluid through electrostatic and electroosmotic force (EOF) [1].

Vacuum The proximal ends of the capillaries may be placed under relative vacuum. The print head and substrate holder may be placed within a vacuum chamber, and the capillaries may extend through a wall of the vacuum chamber and to the reservoirs. The print head in this instance preferably extends to the wall of the chamber so that thin capillaries are not exposed directly to vacuum if no liquid flows through them.

2.2 Flow Rate Control

In order to ensure that the spot sizes on the substrate are constant from microarray to microarray and uniform across each microarray, the flow rate has to be controlled to be constant in each capillary and uniform across the print-head.

It takes routine techniques to hold the fluid flow in a single capillary to a constant rate. All fluid driving methods described in Section 2.2.1 can be used to control the flow rate. Air pressure and gravity are relatively blunt mechanisms for flow rate control. When air pressure or elevation differences disappear, the flow does not stop instantly due to back-pressure built up in the capillary. In comparison, electric fields are more precise in controlling flow rate.

It takes more measures to ensure the uniformity of flow rates in every capillary of the print-head because the flow rate in a capillary is dependent upon many factors besides the driving force, which include cavity size and surface characteristics of the capillary as well as fluid viscosity. Also, clogging and bubble entrapment in capillaries will prevent probe flow and cause unwanted vacancies on the fabricated microarray.

This invention provides the following measures to ensure the flow rate uniformity:

Use of silica based capillaries Silica capillaries are renowned for precise dimensions. Both inner and outer diameters can be controlled to vary less than 2% in a same draw and less than 5% between different draws. (A "draw" is the pulling or stretching of larger, more easily fabricated preforms at a sufficiently high temperature that the tubular preforms thin to form capillaries. This technology is common in optical fiber manufacturing.) Capillaries from the same draw can be used to enhance uniformity of channel diameter in the capillaries. Because the drawing is carried out at melting point of the silica, the surface is extremely smooth. In addition, the silica surface in the capillary is naturally negatively charged, which makes it "phobic" to DNA samples, resulting in minimum friction between DNA probes and capillaries, ensuring smooth delivery of sample fluids to the print-head. Coating cavity walls with other hydrophobic films such as a fluorocarbon polymer such as polytetrafluoroethylene may further enhance the durability and uniformity of the capillaries.

Buffering the probe fluids Different probes may have different viscosity. The viscosity of different probe fluids can be made more uniform by adding a suitable amount of inert buffering material, e.g., sugar, to increase the viscosity of probe fluids of low viscosity.

Clogging and bubble prevention All probe fluids can be purified and handled in a clean room environment to prevent capillary clogging. Fluids can also be preprocessed with ultrasound and vacuum suction to eliminate bubble entrapment.

Figure 7:
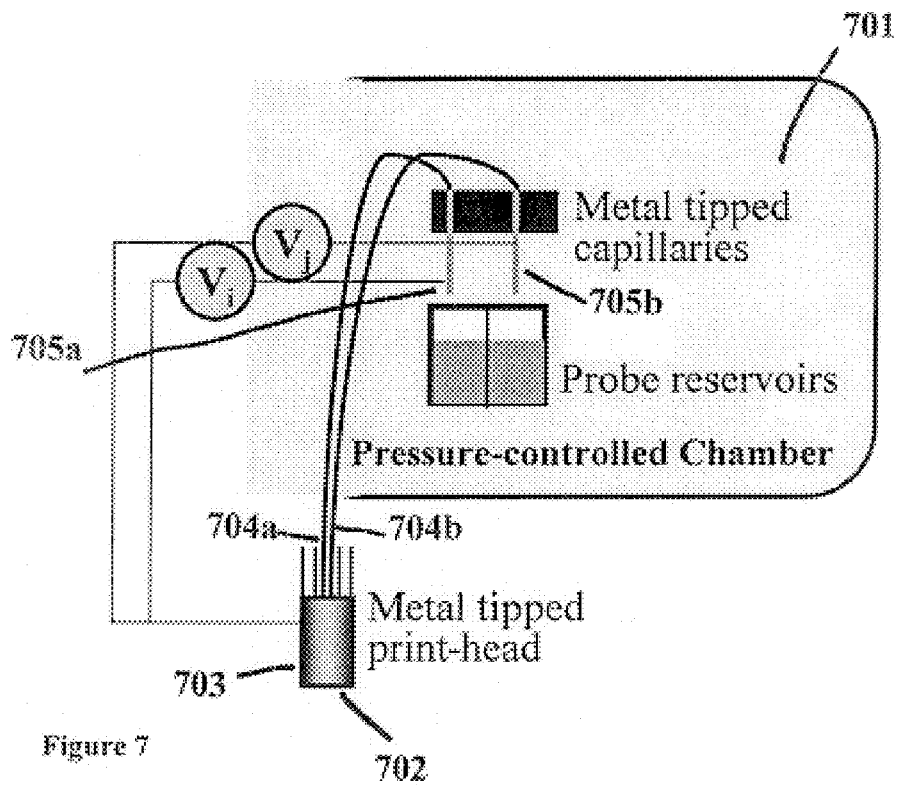
FIG. 7 illustrates two methods of controlling flow rate of probe-containing solution through capillaries, i.e. the use of pressurized gas, and the use of voltage.

Control flow rate in each capillary with individual electric fields The flow rate variation across the print-head can be kept within a small range (e.g. 20%) under a uniform driving force such as air pressure or gravity. This is sufficient when fabricating most microarrays. For applications that require more accurate flow rate control, the electric field method can be used to control the flow rate in each capillary individually. In one specific embodiment of the flow control sub-system, as shown in FIG. 7, gravity and/or pressurized air 701 is used as the primary fluid driving force and an electric field of the original capillary is used as an additional, fine adjustment mechanism. The end-facet 702 of the print-head 703 at the proximal end of the capillaries 704a, 704b, . . . and each capillary tip 705a, 705b, . . . at the distal end of capillaries are coated with metal. All capillaries are held at a common ground at the print-head and different voltages V1, Vj are applied to the different capillary tips at the distal end. This produces appropriate electric fields to fine-tune the flow rate in the capillary. Because the electric field is only a fine-tuning device, a relatively small voltage is sufficient. Voltage can be adjusted based on feedback from inspection devices, as discussed below, or by monitoring the size of droplets deposited using e.g. an optical or scanning microscope.

3. Probe Deposition

The probe deposition sub-system in the arrayer ensures that a constant and uniform volume of probe fluids are deposited onto the substrate and there are minimal or no missing or overlapped spots on the microarray.

3.1 Mechanical Tapping

Figure 8:
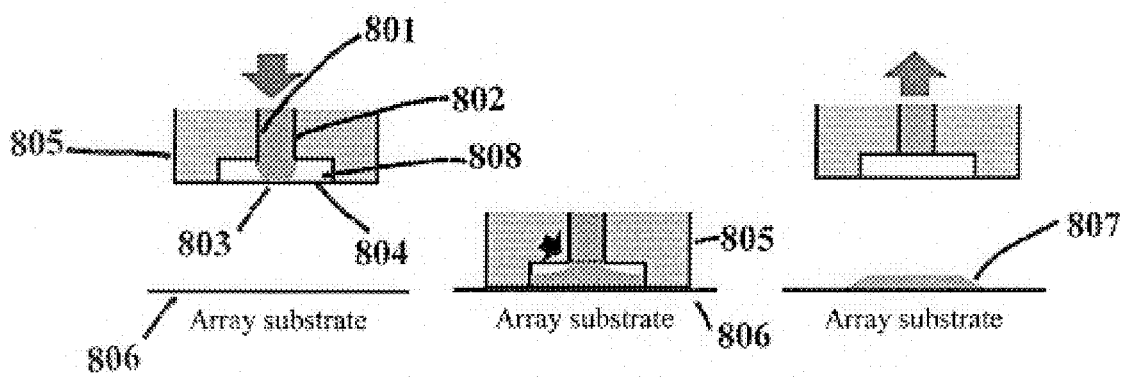
FIG. 8 illustrates probe deposition by mechanical tapping.

As illustrated in FIG. 8, probes can be deposited on to the microarray substrate by mechanically tapping the print-head 805 on the substrate. As shown in FIG. 8a, the constant flow of probe solutions 801 in the capillary 802 produces a micro sphere 803 of fluid at the facet 804 of each capillary. When the print-head 805 is tapped on the substrate 806, the droplet bonds to the substrate due to surface tension as shown in FIG. 8b. This surface tension overcomes the binding force in the fluid. The droplet thus breaks away from the fluid column at its weakest point, i.e. exiting point of the capillary cavity, when the print-head withdraws as shown in FIG. 8c. A probe spot 807 is deposited on the substrate.

Two potential problems associated with microarrays produced with this type of printing method are missing and overlapping probes in the microarray. This invention provides the following measures, which can be used alone or in combination, to prevent missing spots on the fabricated microarray:

1) The distance between the print-head facet and substrate during printing is selected to be no more than the minimum diameter of the probe-containing droplets formed at the tips of the capillaries. Because the radius of the droplets is typically in the order of 10~30 micron, the distance between the print-head facet and substrate is typically in the order of 5 to 20 micron. The surface of the print-head facet is polished to a high degree of flatness when, for example, a microscope slide or other flat substrate is used as the microarray substrate.

Figure 9:
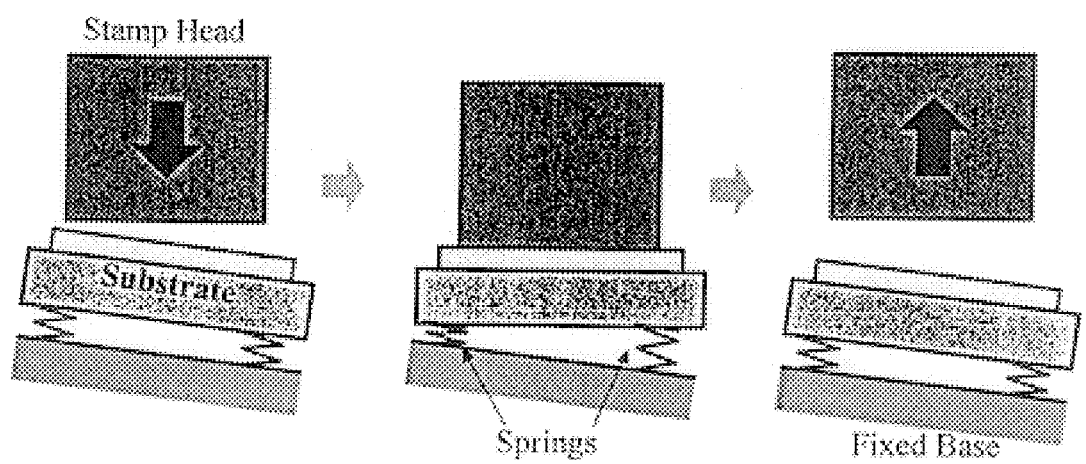
FIG. 9 illustrates a spring-mounted substrate holder that provides improved alignment between substrate and print head.

2) One of the contacting parts, i.e. print-head or the substrate, is rigidly supported while the other is fixed on a soft or spring-loaded platform, as shown in FIG. 9. If these two surfaces are slightly unparallel, the one on the soft support will yield to the one on the rigid mounting to ensure perfect contact (FIG. 9). The platform may be spring loaded, mounted on joints or gimbals, or may be a polymeric or sponge-like block on which the substrate rests, for example.

Probe cross-talk occurs when excess amount of probe fluid is deposited on the substrate and there is a lack of means to confine the deposited fluid within a certain area on the substrate. The flow rate control described in Section 2.2 helps to prevent fluid overflow. In addition, capillary force may be created between the print-head facet and the substrate when the print-head is brought very close to the substrate and a fluid link is established between the two surfaces. This capillary force may act to pull extra fluid out of the cavity. This invention further provides the following measures, which can be used alone or in combination, to prevent overlapping spots on the fabricated microarray:

1) Making both the print-head and substrate surfaces hydrophobic.
2) A micro well 808 can be fabricated at the tip of each capillary (as shown in FIG. 8), which can accommodate the fluid volume of the droplet to be placed on the substrate. The micro wells can be produced one-by-one using a diamond tipped precision drill or in parallel using photolithographic methods. When the capillary has a central region doped with Germanium (originally designed for light transmission as described in Section 2.1.1), these micro wells can be fabricated in parallel by dipping the print-head into an etching fluid such as fluoride acid solution (e.g., HF). A very small amount of Ge doping can dramatically accelerates the etching rate of the silica in the vicinity of the Ge.
3) A spacer can be installed between the print head facet and the surface of the substrate as shown in FIG. 18. During tapping, the spacer face contacts the substrate while the print head facet is suspended closely above the substrate, allowing fluid spheres to contact the substrate to deposit droplets of probe-containing liquid on the substrate.
4) Increase the viscosity of the probe materials to be printed by increasing the sample density in its solution or by adding sufficient amount of inert buffering materials. Print probes in bead, gel or paste forms can eliminate overlapping problem.
5) Reduce the time in which the print-head is in fluid contact with the substrate.
6) Use capillaries with a smaller inner diameter, which will reduce the effect of the capillary pulling force generated in the fluid layer between the print-heat and the substrate during contact printing.
7) Deposit probes on hot substrates in a dry environment, which accelerates the evaporation of fluids in the probe and reduces overflow.
8) Deposit probes on a substrate that has a surface temperature below the freezing point of the probe fluid.

3.2 Electrostatic Printing

Figure 10:
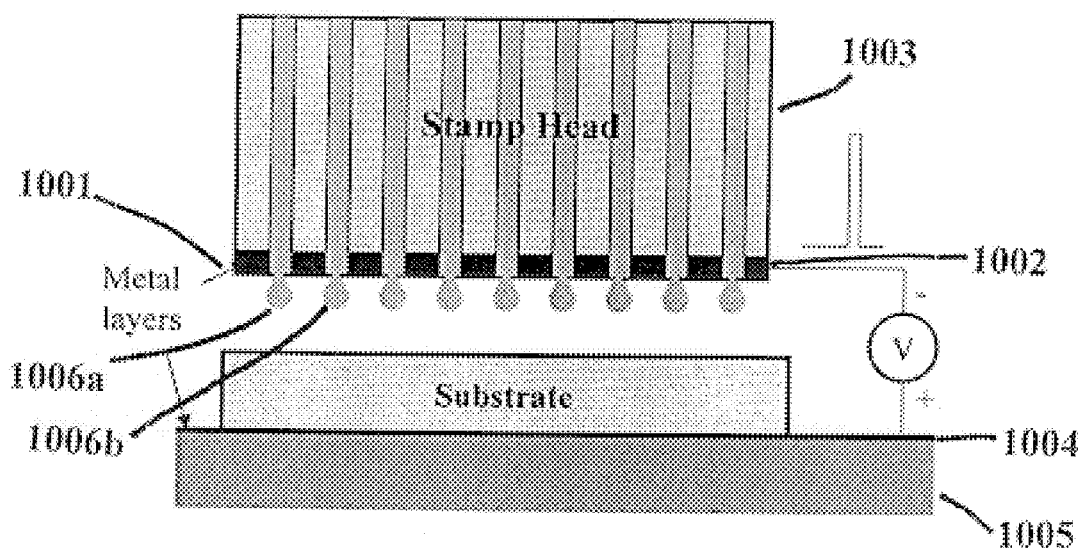
FIG. 10 illustrates probe deposition by electrostatic printing.

As shown in FIG. 10, a conductive layer 1001, such as metal, can be coated on the facet 1002 of the print-head 1003 and the microarray substrate is placed on a conductor 1004 or conductor coated support 1005. Alternatively, a special microarray substrate with conductive layer can be used. When a voltage V is applied between the stamp head and the substrate or its support with positive polarity at the substrate end, the DNA samples in the capillary will be attracted towards the substrate because of their negative charges. If a short pulse of sufficiently high voltage is applied when the stamp head facet is close to the substrate, spots 1006a, 1006b, . . . of the various probe fluids are torn from the fluid columns in the capillaries and are propelled to the substrate. One advantage of this method is that the stamp head does not have to touch the substrate surface, thus eliminating many potential problems associated with missing or overlapping spots on the fabricated microarray. In addition, the stamp head does not have to move, and no microwell is needed at the capillary tip.

3.3 Printing Beads

Probes may also be immobilized on beads and a colloidal suspension formed, and the suspension can be deposited through the capillaries and onto the substrate to deposit the beads onto the substrate. In this event, the beads may be functionalized as described below so that the beads attach to the surface of the substrate. The beads typically have a diameter less than 20 microns, preferably between about 0.1 and 20 micron, and preferably less than 100 nm.

The beads may be transparent, so that the light used to stimulate the fluorescent moieties refracts and reflects a number of times, thereby providing more light to the probes on the illuminated beads to stimulate fluorescence. This leads to a stronger fluorescence signal. Beads are also capable of carrying many more probe molecules on their surfaces than the flat surface of the substrate. Consequently, signal strength also increases because of the large number of target molecules that associate or hybridize to the probe molecules on the surface of the bead.

Figure 17:
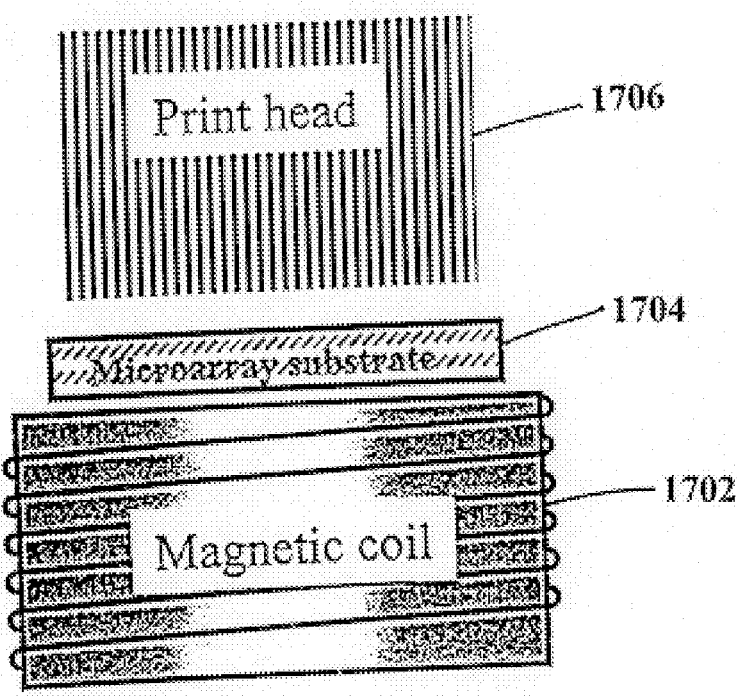
FIG. 17 depicts a print system suitable for depositing probes immobilized on a magnetic support onto a substrate.

The beads may optionally be magnetic or paramagnetic. Magnetic beads are currently commercially available. In this instance, a magnetic field can be established to help drive the magnetic beads from the print head 1706 to the surface of the substrate where they are to be deposited. A suitable magnetic field may be established between the reservoir or the capillaries and the substrate, for instance, by installing a high bandwidth electromagnetic coil 1702 under the microarray substrate 1704 as shown in FIG. 17.

3.4 Electromagnetic Printing

Probe molecules may be attached to ferrofluids (magnetic liquids) to form ferrofluid particles and deposited on the substrate. Ferrofluids are colloidal magnetic particles having a size of about 3 to about 50 $\mu$m (approximately the size of an antibody) and composed of surfactant coated single or multiple crystals of e.g. magnetite ($Fe_3O_4$) dissolved in water or kerosene or other compatible solvent. Alternatively, probe molecules are dissolved or suspended in ferrofluids and not attached to magnetic or paramagnetic particles.

Ferrofluid particles typically have a size ranging from 3 to 100 nm and can be synthesized by a variety of methods which result in 'flocs' composed of polymer (typically dextran or protein) and magnetite and/or other iron oxide crystals. Ligands such as biotin, avidin, streptavidin, or other ligands for attaching the ferrofluids to the substrate may also be coupled to the ferrofluid particles.

The coupling chemistries for attaching antibodies and other relevant molecules such as oligonucleotides to ferrofluids to form ferrofluid particles are known, and molecules coupled to ferrofluids are available from Immunicon Corp., Huntingdon Valley, Pa.

The magnetic properties of ferrofluids derive from the magnetic properties of magnetite and the colloidal nature of the material. Magnetite crystals are typically about 3–10 $\mu$m in size and therefore exhibit superparamagnetism (i.e. they only exhibit magnetic properties when in a magnetic field; when the field is reduced or eliminated, the magnetism disappears).

Ferrofluid particles are easily transported to the substrate surface by applying a magnetic field. The particles can diffuse through solution via Brownian motion and deposit rapidly on the substrate surface. Removing the magnetic field essentially stops the ferrofluid particles from depositing onto the substrate.

3.5 Vacuum Printing

The proximal ends of the capillaries may be placed under relative vacuum in order to draw probe-containing fluid through the capillaries. The print head and substrate holder may be placed within a vacuum chamber, and the capillaries may extend through a wall of the vacuum chamber and to the reservoirs which are at atmospheric pressure. The print head in this instance preferably extends to the wall of the chamber so that thin capillaries are not exposed directly to vacuum if no liquid flows through them. The pressure in the vacuum chamber can be reduced to below atmospheric pressure to draw fluid from the reservoirs and print on the substrate, and the pressure in the vacuum chamber can be increased to about or slightly above atmospheric pressure to prevent further fluid from depositing on the substrate when the print head is lifted away from the substrate.

3.6 Probes

The probes may be DNA, RNA, proteins, cells, or other constituents as discussed previously. The probes may be attached to the substrate or to beads covalently. Thus, one may use a variety of approaches to bind an oligonucleotide to the solid substrate. By using chemically reactive solid substrates, one may provide for a chemically reactive group to be present on the nucleic acid, which will react with the chemically active solid substrate surface. One may form silicon esters for covalent bonding of the nucleic acid to the surface. Instead of silicon functionalities, one may use organic addition polymers, e.g. styrene, acrylates and methacrylates, vinyl ethers and esters, and the like, where functionalities are present which can react with a functionality present on the nucleic acid. Amino groups, activated halides, carboxyl groups, mercaptan groups, epoxides, and the like, may also be provided in accordance with conventional ways. The linkages may be amides, amidines, amines, esters, ethers, thioethers, dithioethers, and the like. Methods for forming these covalent linkages may be found in U.S. Pat. No. 5,565,324 and references cited therein.

Alternatively, the probes may be attached to the substrate or to beads non-covalently by e.g. functionalizing the surface of the substrate and the probe to provide binding moieties on each. Generally, this will be accomplished by providing each of the probe and the support with one of a pair of corresponding affinity binding partners, such that the probe and the support may be bound together selectively, and if desired, reversibly. Typical non-covalent coupling agents include biotin/streptavidin, *Staphylococcus aureus* protein A/IgG antibody $F_C$ fragment, and streptavidin/ protein A chimeras. See, e.g., T. Sano and C. R. Cantor, Bio/Technology 9:1378–81, 1991. Most conveniently, the affinity binding partner will comprise biotin and avidin or streptavidin, the biotin being bound to the probe and the avidin or streptavidin to the support. In such an embodiment, the surface of the substrate may be functionalized with avidin or streptavidin, and the probe molecules may be functionalized with biotin by methods well-known in the art. See, e.g., U.S. Pat. No. 5,948,624 and "Applications of Avidin-Biotin Technology: Literature Survey," by Wilchek, M., and Bayer, E. A., Methods in Enzymology, vol. 184, pp. 14–45, 529–537, 588–600 (1990) which are incorporated herein by reference in their entirety. Both biotin-labeled oligonucleotide probes and streptavidin-coated particles are commercially available (Dynal AS). Alternatively, the probe and the support may be bound together non-selectively and reversibly. One of the most commonly used techniques for immobilizing DNA onto glass microscope slide is to coat the slides with polylysine as discussed by, e.g., Schena M, Shalon D, Davis R W, Brown P O, *Quantitative monitoring of gene expression patterns with a complementary DNA microarray*, Science 270(5235):467–70 (Oct. 20, 1995). Most commercially produced slides have positively charged amino-silane surface chemistry. These slides are prepared by reacting activated glass slides with different silanes, leading to the covalent addition of positively charged primary amine groups free to attract negatively charged sugar phosphate backbone of cDNA. Newly developed immobilization methods included end point, covalent attachment of amine- or thiol-modified oligonucleotides and PCR products to the amine- or thiol-reactivating groups on glass surfaces as discussed in, e.g., Beier M, Hoheisel J D, *Versatile derivatisation of solid support media for covalent bonding on DNA-microchips*, Nucleic Acids Res. 27(9):1970–7 (May 1, 1999) and Rogers Y H, Jiang-Baucom P, Huang Z J, Bogdanov V, Anderson S, Boyce-Jacino M T, *Immobilization of oligonucleotides onto a glass support via disulfide bonds: A method for preparation of DNA microarrays*, Anal Biochem. 266(1):23–30 (Jan. 1, 1999). In addition, nitrocellulose solution containing DNA has been used to form DNA microarrays, as discussed in, e.g., Pinkel D, Segraves R, Sudar D, Clark S, Poole I, Kowbel D, Collins C, Kuo W L, Chen C, Zhai Y, Dairkee S H, Ljung B M, Gray J W, Albertson D G, *High resolution analysis of DNA copy number variation using comparative genomic hybridization to microarrays*, Nat Genet. 20(2):207–11 (October 1998). All above method can be used to link DNA to glass surface under current configuration.

Beads may also be attached to the surface of the substrate either covalently or non-covalently as described above. Beads may also be attached to the surface by functionalizing the end of probe molecules, so that some of the probes bind the beads to the substrate surface.

Oligonucleotide probes of the invention are affixed, immobilized, provided, and/or applied to the surface of the solid support using any available means to fix, immobilize, provide and/or apply oligonucleotides at a particular location on the solid support. The various species may be placed at specific sites using ink jet printing (U.S. Pat. No. 4,877, 745), photolithography (See, U.S. Pat. Nos. 5,919,523, 5,837,832, 5,831,070, 5,770,722 and 5,593,839), silk printing, offset printing, stamping, mechanical application with micropipets using an x-y stage or other rastering technique, or any other method which provides for the desired degree of accuracy and spatial separation in placing the bound component.

Combinatorial array approaches, such as described by Southern et al. (U.S. Pat. Nos. 5,770,367, 5,700,637, and 5,436,327), Pirrung et al. (U.S. Pat. No. 5,143,854), Fodor et al. (U.S. Pat. Nos. 5,744,305 and 5,800,992), and Winkler et al. (U.S. Pat. No. 5,384,261), have been used with success in cases in which polymers of short sequences are required. In these "GeneChips," oligonucleotide probes (20–25-mers) or peptide nucleic acids (PNAs) are produced either in situ during microarray fabrication, or offline using traditional methods and spotted on the microarrays. U.S. Pat. Nos. 5,445,934 and 5,744,305 to Fodor et al. describe the manufacture of substrates containing multiple sequences at density of 400 different probes per square centimeter or higher. These chip are synthesized using solid-phase chemistry and photolithographic technology. The combinatorial approaches generate significant biological and chemical diversity but are unable to construct microarrays of large macromolecules and can also be expensive and difficult to implement.

Ink jet dispenser devices are used to deposit small drops of liquid on a solid substrate. The fabrication of biological and chemical arrays by such technology has been shown by Brennan (U.S. Pat. No. 5,474,796), Tisone (U.S. Pat. No. 5,741,554), and Hayes et al. (U.S. Pat. No. 5,658,802). These non-contact technologies are unable to array large numbers of samples easily and to control the quality of the resultant microarrays.

A third category of arraying devices work by direct surface contact printing as described by Augenlicht (U.S. Pat. No. 4,981,783), Drmanac et al. (U.S. Pat. No. 5,525,464), Roach et al. (U.S. Pat. No. 5,770,151), Brown et al. (U.S. Pat. No. 5,807,522) and Shalon et al. (U.S. Pat. No. 6,110,426). In this format, the probes are long complementary DNAs (cDNAs) 500–5000 bases long, synthesized by traditional methods before immobilization. Deficiencies of such technologies as quill-based spotters include imprecise sample uptake and delivery as well as lack of durability.

Martinsky et al. (U.S. Pat. No. 6,101,946) describe the use of an electronic discharge machine (EDM) which can be attached to a motion control system for precise and automated movement in three dimensions. The oligonucleotide primers may also be applied to a solid support as described in Brown and Shalon, U.S. Pat. No. 5,807,522 (1998). Additionally, the primers may be applied to a solid support using a robotic system, such as one manufactured by Genetic MicroSystems (Woburn, Mass.), GeneMachines (San Carlos, Calif.) or Cartesian Technologies (Irvine, Calif.).

4. Array Inspection

The array inspection sub-system monitors the quality of fabricated microarrays. This can be carried out off line or online and in real-time. Arrays with missing and overlapped spots are automatically detected, registered and eventually rejected as defect products. The device may also be used to monitor the spot sizes in real time and feed the information back to the fluid delivery sub-system to control the flow rate in the capillaries. If the spot sizes are uniformly too large or small in the print-head, the system has the option to adjust the printing rate accordingly to compensate for the spot size change by e.g. adjusting the voltage applied to the individual capillaries.

This invention offers two different optical designs for the inspection subsystem.

Figure 11:
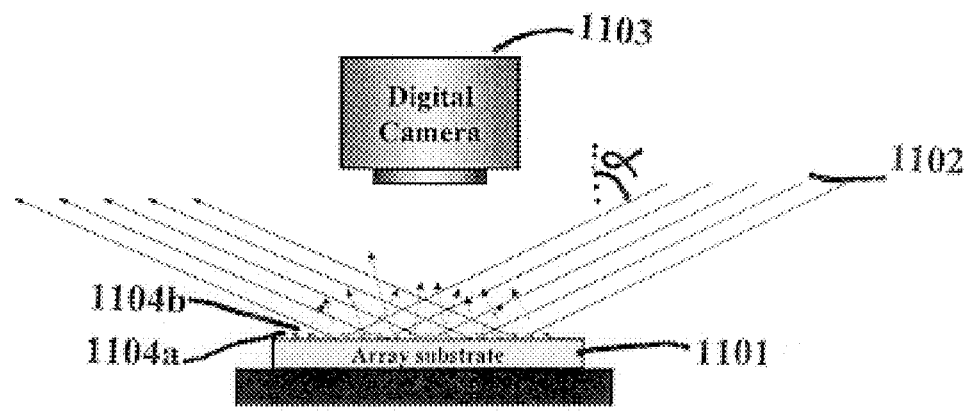
FIG. 11 illustrates equipment for and a method for inspecting a microarray using light-scattering.

The first design, shown in FIG. 11, is based on the detection of light scattered by the spots on the microarray. A fabricated microarray 1101 is illuminated with light project at a large angle α. A digital camera 1103 observes the substrate surface from above. Due to their small fluid volume, probes 1104a, b, . . . deposited on the substrate will dry almost instantly and a high salt content in the probe fluid solution deposits. The salt is present in a sufficient amount to scatter light that shines upon it. At areas on the substrate where there are no spots, there is no salt to scatter the light and therefore the light is reflected at the same large angle to the side. The camera registers a dark background in these areas. At areas where there is a spot, the salt scatters the light towards the camera, and the camera registers bright spots where probes are deposited.

Figure 12:
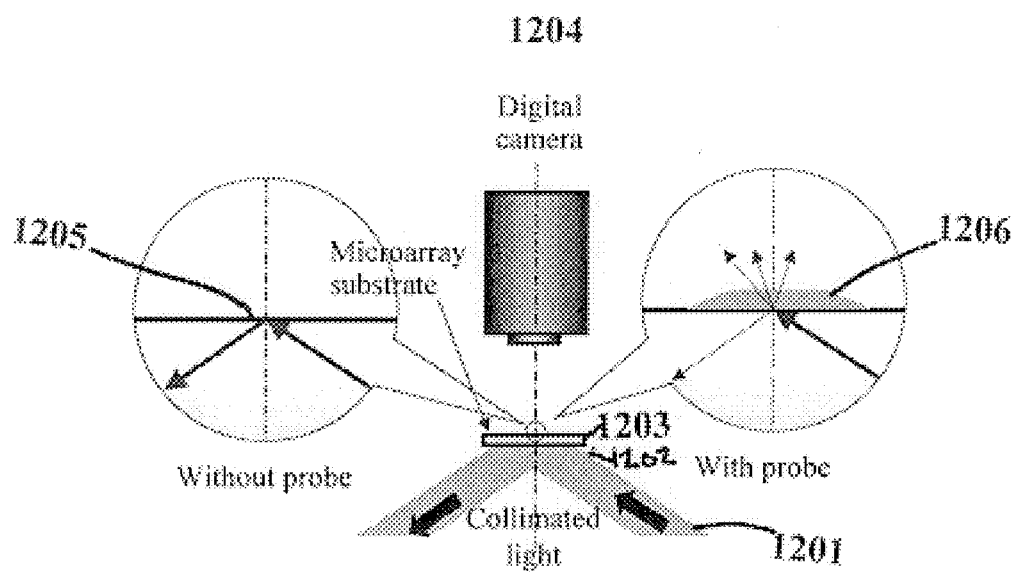
FIG. 12 illustrates equipment for and a method for inspecting a microarray using total internal reflection of light within the substrate.

The second design, shown in FIG. 12, is based on the principle of total internal reflection and is suitable for the inspection of spots where there is nothing in spots that scatters sufficient light to register it. A collimated light beam 1201 is projected to the bottom surface 1202 of the slide 1203 on which the probe microarray is deposited. The angle of incidence to the bottom surface 1202 is slightly larger than the critical angle of total internal reflection at the substrate-to-air interface. A digital imaging camera 1204 is used to observe the illuminated region above the substrate surface. In an area 1205 of the surface where there is no probe, total internal reflection occurs and little light can be detected by the camera pixel aimed at this location. However, the presence of the probe 1206 destroys the condition of total internal reflection at the substrate-air interface. Part of the light beam will be refracted into the space above the substrate surface and captured by the imager. This method can significantly increase the contrast of most transparent objects.

5. Spatial Pattern of the Spots on the Microarray Substrate

Figure 13:
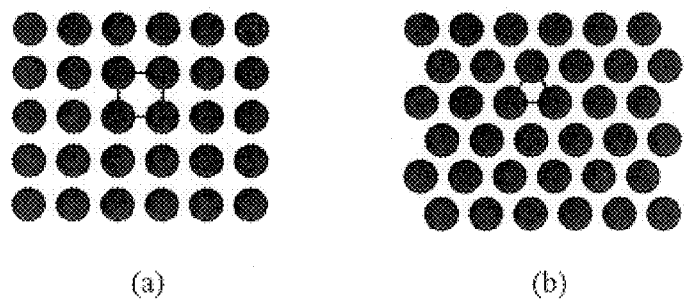
FIG. 13 illustrates two ordered spot patterns that can be formed when individual fibers are used to form a print head using a guide plate.

The "chessboard" spatial pattern as shown in FIG. 13a is the most common microarray format on the market. This pattern arises because of the prevalent manufacturing method of making these microarrays. Photolithography is used to build oligomeric sequences in situ, on the substrate, and the x-y positioning stage of the fabrication equipment is configured to provide an orderly matrix in a chessboard pattern. An inkjet print system is expected to also produce a chessboard pattern of spots.

Because a probe microarray of this invention is produced in a printing process, the spatial pattern of the probes on the substrate is identical to the pattern of the capillary facets in the print-head. As described above, the printhead can be fabricated by two different methods, i.e. the guide plate and the random tight bundle. These two methods provide great flexibility in the probe pattern of the microarray.

When the guide plate method is used to fabricate a print head, the spatial pattern of the capillaries is determined by that of the holes in the guide plate. The capillaries and therefore the probe pattern can be a highly organized matrix in either a chessboard pattern as shown in FIG. 13(a) or a honeycomb pattern as shown in FIGS. 13(b) and 15. In a honeycomb matrix, the centers of every three adjacent spots form an equilateral triangle 1501, and six spots surrounding any spot form a hexagon 1502. In addition, spots align in straight lines globally across the entire microarray, as illustrated by lines 1503 and 1504. Consequently, the microarray of probes is formed of rows of probe spots, where the probes of every other row (e.g. row n, n+2, n+4, etc. where n=1 or n=2) are also aligned in columns, but an adjacent row is shifted so that a probe of one row lies between two probes of the next row (i.e. the majority of probes of row n are centered between the probes of row n+1).

When the random tight bundle method is used to make a print head, the spot pattern appears well organized locally, i.e. it is still generally true that centers of three adjacent spots form an equilateral triangle 1601, and six spots surrounding a spot form a hexagon 1602 as illustrated in FIG. 16. However, globally, the spatial pattern becomes random. Spots across the microarray no longer form a true array but become shifted compared to one another, as illustrated by lines 1603 and 1604 in FIG. 16. This is because that in a tight pack, capillaries take up positions in reference to each other. This preserves the order of local spatial pattern. However, minute misalignments among capillaries soon accumulate distorting the global alignment of the spots. With the increase in the number of spots, such distortions can grow worse and worse. Eventually, there is no global alignment for spots across the array, or there are localized regions of order with discontinuous regions between the ordered regions. The global spatial pattern becomes more random than is the case with an ordered microarray.

When the capillaries are not tightly packed, even the local spatial pattern illustrated in FIG. 16 may not be preserved. The probe positions throughout the microarray can be completely random.

It is highly unlikely that a first random bundle of capillaries, made either by tightly packing the capillaries or by loosely packing the capillaries, will be identical to a second random bundle of capillaries formed of identical capillaries. The consequence of this is twofold. First, the print face of the first random bundle is not identical to the print face of the second random bundle. Consequently, a microarray pattern formed by the probes printed using the first random bundle will not be identical to the microarray pattern formed by the probes printed using the second random bundle.

Second, the position of a particular probe in the first microarray is likely to differ significantly from the position of that probe in the second microarray. The positions of both the distal and proximal ends of a single capillary in a first random bundle comprised of thousands of capillaries is unlikely to be the same in a second bundle formed of identical capillaries. As a consequence, a microarray containing identical probes but printed using the first print head is likely to have the probes in an entirely different arrangement of probes from a microarray printed with the second print head. As discussed previously, the registry of probes to reservoirs performed by, e.g., launching light into the reservoirs to correlate proximal and distal ends of the capillaries, is used to determine the positions of probes in the microarray.

A microarray printed using a random bundle may have software associated with it that provides data which correlates the identity of the target or probe molecules with a particular location on the substrate or within the microarray, as discussed above. The software may be provided as a database providing this correlation and may be on a portable medium such as a CDROM or may be downloaded to a user's equipment via a telephone line, cable modem, satellite link, or other form of data communication. The software is loaded into a computer or into dedicated equipment associated with a scanner, so that the hybridization pattern read by the scanner can be translated into information on the target molecules or probe molecules that have hybridized (or otherwise associated) on the substrate.

6. Other Potential Benefits of Light Guiding Capillaries

Light guiding capillaries have other important utilities in the microarray fabrication. For example, the microarray substrate can be coated with a layer of light sensitive material, which is hydrophobic in the dark and becomes hydrophilic after exposure to light. Examples of this material include O-carboxymethylated calyx resorcinaren, or other compounds containing photochromic azobenzenes. A light pulse can be sent down the capillary at the very moment that the print head deposits the probe microarray onto the substrate. It will make the region immediately under the micro-fluid well at each capillary tip hydrophilic while leaving the rest of the substrate surface hydrophobic. In this way, not only the probe will be confined to a well-defined area, target sample fluid will also concentrate in the probe region during the hybridization stage, which helps to improve hybridization efficiency and reduce the required amount of target fluid. One may also choose the appropriate substrate coating material and light wavelength, so that the substrate-probe cross-linking can occur instantly when the probe is laid down in fluid phase. The substrate includes, in one aspect, a glass support, a coating of a polycationic polymer, such as polylysine or polyarginine on the surface of the support, and a microarray of distinct polynucleotides electrostatically bound non-covalently to said coating, where each distinct biopolymer is disposed at a separate, defined position in a surface microarray of polynucleotides.

Since optic fiber capillaries can transmit near UV light, photoimmobilization can also be used to covalently link biopolymers such as DNA, protein or other substances to a substrate support such as a glass surface. Photophores such as benzophenone derivatives can be anchored to the silica surface using an established method such as that disclosed by Ayadim M and Soumillion J P, *Photosensitizers covalently anchored to the silica surface: modulation of the excited state efficiency through electron transfer from the linking arm or from the surface*, Tetrahedron Letters, 1995, Vol. 36, pp. 4615–4618. When soluble DNA or proteins are printed onto the glass slide, a near UV light-irradiation can be launched through the optic fiber capillaries to initiate the covalent attachment of DNA or protein to the glass surface. Alternatively, photophores can be conjugated with DNA or proteins first, then photoimmobilized to the glass surfaces upon photo-irradiation as discussed in, e.g., Dorman G and Prestwich G D, *Using photolabile ligands in drug discovery and development*, Trends Biotechnol. 8(2):64–77 (February 2000).

Light guiding capillaries can be used to incorporate photon cleavable linkers in the probe samples and alter the molecular structures of certain probe or to prevent the fragment from entanglement when they are being laid. For example, streptavidin- or avidin- to biotin interaction can be cleaved by a laser. A photolabile cross-linker such as 3-amino-(2-nitrophenyl) propionic acid (Brown et al. Molecular Diversity 4–12 (1995) and Rothschild et al. Nucleic Acids Res. 24:351–66 (1996)) can be employed to provide a means for cleaving a nucleic acid from the solid support, if desired. For further examples of cross-linking reagents, see, e.g., S. S. Wong, "Chemistry of Protein Conjugation and Cross-Linking," CRC Press (1991), and G. T. Hermanson, "Bioconjugate Techniques," Academic Press (1995) and U.S. Pat. No. 5,900,481.

Light guiding capillaries can also be used to activate chemical reactions within the probe by illuminating the probe microarrays at certain conditions. G Protein Coupled Receptors (GPCRs) suitable for use in the present invention are those in which agonist binding induces G protein-coupled receptor kinase (GRK) phosphorylation and subsequent translocation of arrestin from the cytosol of the cell to the cell membrane, as in light-activated GPCRs, such as rhodopsin.

In addition, light guiding capillaries can be used to conduct spatially addressable combinatorial synthesis of oligonucleotide or peptide libraries under the current invention. One feature of this parallel synthesis technique is the combination of photolabile protecting groups and lithography. It allows a pattern-directed photolytic cleavage in each cycle, followed by a coupling reaction with a new amino acid or a new nucleotide, protected, again with photolabile groups. The sequence diversity is generated by the different patterns in each cycle. In traditional photolithographic method, such pattern is generated through the use of photomasks. Under the current invention, photolytic cleavage can be induced at desired spots by shining light through selected, individual capillaries from the distal end. This method avoids the most expensive and time-consuming steps of making photomasks in the traditional method utilizing photolithography.

Furthermore, light guiding capillaries and/or a microarray of the current invention can be used as a high throughput screening device for drug discovery. The device can be used to conduct massive parallel solid-phase combinatorial synthesis of chemical compounds. Such chemical compound libraries can be used to screen for drug leads or for lead optimization. Alternatively, a massive number of pre-synthesized chemical compounds can be arrayed and screened using capillaries, bundles, print systems, and methods of the current invention. For example, a library of chemical compounds can be arrayed and photo-immobilized. The compounds can be screened for their ability to bind a target or to modulate the activity of a target. The target could be a protein or DNA or any substance known to be involved in any disease process.

Under the current invention, one can determine the targets of compound libraries. Photolabelling groups can be covalently attached to compound libraries and photoaffinity labeling could be carried out to identify interacting targets. The interacting targets could be proteins or DNA or other substances.

7. Additional Applications of the Disclosed Invention

Figure 14:
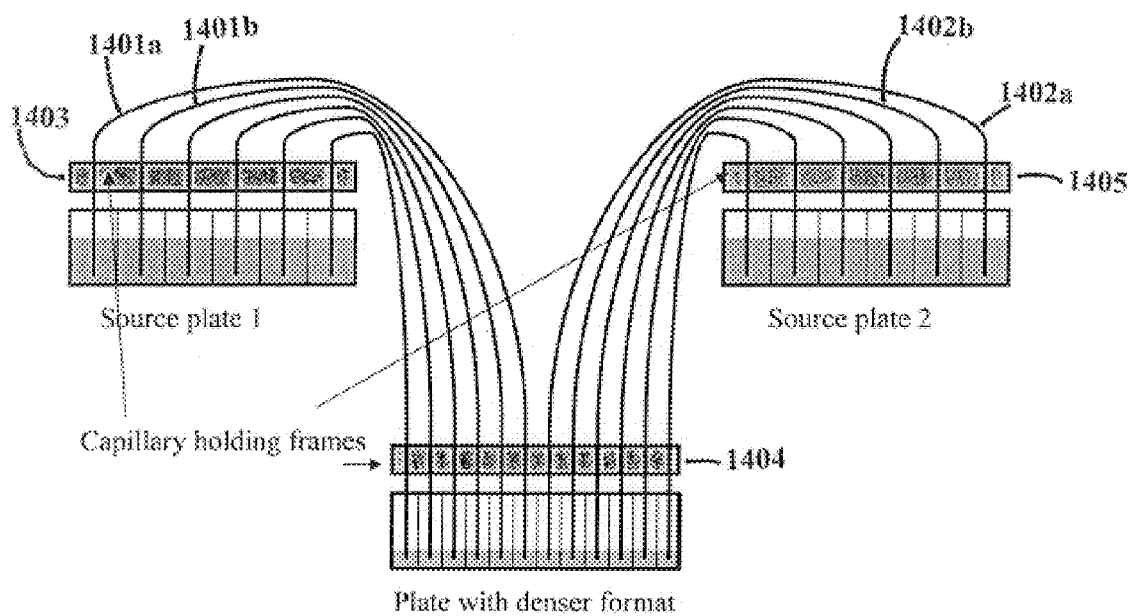
FIG. 14 illustrates how a fluid transfer device composed of multiple capillary bundles can be configured to draw liquid from multiple microtiter plates having wells of large capacity and place that liquid in small reservoirs contained in a single microtiter plate.

Microtiter plates are the most widely used device for the storage, transport and handling of chemical or biological samples or used as reaction vessel to perform multiple chemical or biological reactions in parallel. In addition to the application of microarray fabrication described above, a capillary bundle of the invention can be adapted to transport biological and chemical samples from one or multiple microtiter plates to other locations in a laboratory test system. In particular, it is ideally suited to transfer samples between a standard microtiter plate to other multi-well or multi-channel devices or between standard microtiter plates with the same or different formats (for example from 96-well plate to 364-well plate and vise versa). In this application, multiple flexible capillaries 1401 *a*, 1401*b*, . . . are attached to two frames 1403 and 1404, respectively, one at each end, as shown in FIG. 14. The frame at one end holds the capillaries in the same spatial pattern and pitch as the wells in the microtiter plate that is the source of the sample while the frame at the other end holds the opposite ends of the capillaries in the same spatial pattern and pitch as the wells in the destination plate. A frame for higher density plate (1404) can be linked to multiple frames (1403 and 1405) for lower density plates in this way. For example, a capillary frame for 364-well microtiter plates fixes 364 capillary terminals into a 16×24 matrix. It can be linked to four frames for 96-well microtiter plates, each of which forms a 8×12 capillary matrix. To implement sample transfer, frames that hold capillaries are locked onto the source and destination plates respectively so that capillary terminals are plugged into its respective wells. Source plate or plates together with the capillary matrix are put into a pressure chamber. A positive pressure will drive the samples from the source plate to the destination plate. Alternatively, the destination plate or plates can be placed in the pressure chamber and a negative pressure is applied to achieve the sample transfer.

A light-conducting capillary or capillary bundle can be used for any application in which it is desirable to transport light and fluid simultaneously. For example, information can be encoded on a substrate at the same time that a microarray is printed by inducing a change in a photo-sensitive chemical layer on the substrate during microarray printing or before or after a microarray is printed. A light-conducting capillary or capillary bundle can also be used to deliver both a photodynamic therapy drug and its activating light to a treatment site on or in a patient's body. Further, fluid and information encoded in light can be simultaneously transmitted through a light-conducting capillary or capillary bundle. In the telecommunications field, optical fibers carry light signals of various wavelengths (channels). Light of each wavelength is individually modulated to encode information in the form of light pulses. A light-conducting capillary allows the simultaneous transmission of a fluid (gaseous or liquid) and one or more data channels, either individually or multiplexed.

A light-conducting capillary can be constructed by forming a waveguide structure through the capillary which is made of a material that is transparent to the light and has a refractive index higher than a cladding material surrounding the waveguide. Such a structure may be formed in many ways. One way is to make a capillary of silica and coat the outer surface of the capillary with a polymer of lower refractive index along the length of the capillary. Another way is to form the capillary of a material having a single refractive index that is selected so that light transmitted into the distal end of the capillary is conducted through the capillary to exit at the proximal end of the capillary. In this instance, air may form the cladding. A third way of forming a light-conducting capillary is to form the capillary of a material (a polymer, for example) having a refractive index lower than that of the fluid to be transmitted through the capillary. The fluid then acts as the core, and the capillary acts as the cladding. Consequently, light transmitted into the fluid at the distal end of the capillary reflects off the channel wall of the capillary and exits the fluid at the proximal end of the capillary. A fourth way to form a light-conducting capillary has been described previously, which is to deposit a layer of Ge or Al doped silica along the cavity wall of a silica preform (the Ge or Al doped silica having a higher refractive index than the material from which the preform is made), and stretching the preform to form the light-conducting capillary. A fifth way is to deposit a layer of Fluoride or Boron doped silica outside a pure silica tube preform (F or B doping lowers the refractive index of the silica), and then extrude or draw the preform to form the light conducting capillary.

What is claimed is:

1. A capillary bundle comprising a plurality of individual capillaries having proximal and distal ends, each of said capillaries having a wall defining a channel extending from the proximal end to the distal end of the capillary, wherein said proximal ends of the individual capillaries are secured to one another in a solid mass of a static array containing capillaries at a density of at least about 83 capillaries per square centimeter, and the proximal ends of the individual capillaries terminate within about 100 microns of one another.

2. A capillary bundle according to claim 1, wherein said proximal ends of the individual capillaries terminate within about 20 microns of one another.

3. A capillary bundle according to claim 1 or 2, wherein said plurality of capillaries comprises a light-conducting capillary that transports light from the distal end to the proximal end of the capillary.

4. A capillary bundle according to claim 1, wherein said plurality of capillaries are secured to one another to form a random bundle so that the distal ends of the capillaries are grouped in a first arrangement, the proximal ends are grouped in a second arrangement, and the first arrangement is not identical to the second arrangement.

5. A capillary bundle according to claim 1, wherein said bundle comprises at least about 1000 capillaries.

6. A method of printing a microarray comprising passing a plurality of liquids containing biological materials though the plurality of individual capillaries of a capillary bundle according to claim 1, and printing said microarray on a substrate.

7. A method of printing according to claim 6, wherein said plurality of capillaries comprises a light-conducting capillary that transports light from the distal end to the proximal end of the capillary.

8. A method according to claim 6, wherein said plurality of capillaries are secured to one another to form a random bundle so that the distal ends of the capillaries are grouped in a first arrangement, the proximal ends are grouped in a second arrangement, and the first arrangement is not identical to the second arrangement.

9. A capillary bundle comprising a plurality of light-guiding capillaries, each of said plurality of light-guiding capillaries having a wall defining a channel and said wall comprising a region of high refractive index surrounded by a region of lower refractive index along the length of the capillary, wherein each of said plurality of light-guiding capillaries is capable of transporting light and a liquid from a distal end to a proximal end of the capillary simultaneously and the proximal ends of said plurality of light-guiding capillaries are bundled together and contain capillaries at a density of at least about 83 capillaries per square centimeter.

10. A capillary bundle according to claim 9, wherein each of said plurality of light-guiding capillaries contains a liquid comprising a biological material selected from the group consisting of deoxyribonucleic acids, ribonucleic acids, synthetic oligonucleotides, antibodies, cells, tissue, proteins, peptides, lectins, fluorophores, chromophores, chelates, haptens, and drug compounds.

11. A capillary bundle according to claim 9, wherein each of said plurality of light-guiding capillaries has an outer diameter of less than 200 microns.

12. A capillary bundle according to claim 9, wherein said bundle comprises at least about 1000 capillaries.

13. A capillary bundle according to claim 9, wherein each of said plurality of light-guiding capillaries has an outer diameter of less than about 300 micron.

14. A capillary bundle according to claim 9, wherein each of said plurality of light-guiding capillaries has an outer diameter of less than about 100 micron.

15. A capillary bundle according to claim 9, wherein each of said plurality of light-guiding capillaries comprises doped silica.

16. A capillary bundle according to claim 1, wherein each of said plurality of capillaries has an outer diameter of less than about 300 micron.

17. A capillary bundle according to claim 1, wherein each of said plurality of capillaries has an outer diameter of less than 200 micron.

18. A capillary bundle according to claim 1, wherein each of said plurality of capillaries has an outer diameter of less than about 100 micron.

19. A method of printing according to claim 6, wherein said proximal ends of the individual capillaries of the capillary bundle terminate within about 20 microns of one another.

20. A method of printing according to claim 6, wherein said bundle comprises at least about 1000 capillaries.

21. A method of printing according to claim 6, wherein each of said plurality of capillaries has an outer diameter of less than about 300 micron.

22. A method of printing according to claim 6, wherein each of said plurality of capillaries has an outer diameter of less than 200 micron.

23. A method of printing according to claim 6, wherein each of said plurality of capillaries has an outer diameter of less than about 100 micron.

24. A method of printing according to claim 6, wherein each of said liquids comprises a biological material selected from the group consisting of deoxyribonucleic acids, ribonucleic acids, synthetic oligonucleotides, antibodies, cells, tissue, proteins, peptides, lectins, fluorophores, chromophores, chelates, haptens, and drug compounds.

* * * * *